United States Patent [19]

MacLeay et al.

[11] 3,931,143

[45] Jan. 6, 1976

[54] UNSYMMETRICAL ALIPHATIC MONOAZO COMPOUNDS

[75] Inventors: Ronald Edward MacLeay, Williamsville; Chester Stephen Sheppard, Tonawanda, both of N.Y.

[73] Assignee: Pennwalt Corporation, Philadelphia, Pa.

[22] Filed: June 1, 1971

[21] Appl. No.: 149,061

Related U.S. Application Data

[63] Continuation-in-part of Ser. No. 725,180, April 29, 1968, abandoned, which is a continuation-in-part of Ser. No. 616,158, Feb. 15, 1967, abandoned.

[52] U.S. Cl. .............. 260/192; 260/88.3; 260/89.1; 260/89.3; 260/89.5; 260/91.5; 260/92.8; 260/93.5; 260/93.7; 260/94.2; 260/94.9; 260/864; 260/465 E; 260/465.5 A; 260/566 B
[51] Int. Cl.² ........................... C07C 107/02
[58] Field of Search .................... 260/192

[56] References Cited
UNITED STATES PATENTS

| | | |
|---|---|---|
| 2,492,763 | 12/1949 | Pinkey ............................ 260/192 X |
| 2,515,628 | 7/1950 | Castle ................................ 260/192 |
| 2,586,995 | 2/1952 | Robertson .......................... 260/192 |
| 2,599,299 | 6/1952 | Upson ................................ 260/192 |
| 2,605,260 | 7/1952 | Johnson ......................... 260/192 X |
| 2,711,405 | 6/1955 | Anderson ........................... 260/192 |
| 2,778,818 | 1/1957 | Hyson et al. ....................... 260/192 |
| 3,309,297 | 3/1967 | Takayama et al. ............. 260/192 X |
| 3,350,385 | 10/1967 | Spialter ............................. 260/192 |

FOREIGN PATENTS OR APPLICATIONS

| | | |
|---|---|---|
| 724,144 | 12/1965 | Canada .............................. 260/192 |
| 374,700 | 3/1964 | Switzerland ....................... 260/192 |

OTHER PUBLICATIONS

Wagner & Zook, *Synthetic Organic Chemistry*, John Wiley & Sons, Inc., New York, 1953, pp. 591–594.

*Primary Examiner*—Charles F. Warren
*Attorney, Agent, or Firm*—David Edwards

[57] ABSTRACT

Unsymmetrical azo compounds:

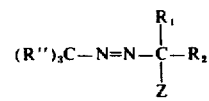

where $(R'')_3C-$ is tertiary-aliphatic and Z is cyano or a derivative thereof, e.g., 2-t-butylazo-2-cyanopropane; processes for preparing such azo compounds by (a) adding hydrocyanic acid to a preformed hydrazone,

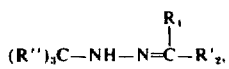

of a ketone to form a hydrazo compound, and oxidizing the hydrazo compound; or (b) oxidizing the hydrazo compound formed by the reaction of a t-aliphatic hydrazine with hydrogen or alkali metal cyanide in water.

13 Claims, No Drawings

UNSYMMETRICAL ALIPHATIC MONOAZO COMPOUNDS

RELATED APPLICATIONS

This application is a continuation-in-part of our copending application Ser. No. 725,180, filed Apr. 29, 1968 (now abandoned), which is a continuation-in-part of our application Ser. No. 616,158, filed Feb. 15, 1967 (now abandoned).

BACKGROUND OF THE INVENTION

This invention relates to unsymmetrical t-aliphatic ("t"=tertiary) alpha-cyano-azo (and hydrazo) alkanes, their derivatives, processes for preparing same and processes utilizing such azo compounds as polymerization initiators.

Symmetrical azo compounds having a t-carbon atom joined to each azo nitrogen and symmetrical alpha, alpha'-dicyano-azo(and hydrazo) alkanes are known:

E. Farenhorst and E. C. Kooyman, Rec. Trav. Chim. 72, 993 (1953).

C. G. Overberger et al., J. Am. Chem. Soc., 76, p. 2722, p. 6185 (1954); ibid. 75, 2078 (1953).

T. E. Stevens, J. Org. Chem. 26, 2531 (1961).

S. F. Nelson et al., J. Am. Chem. Soc. 88, 137, 143 (1966).

Unsymmetrical azo compounds where a t-carbon atom is joined to one azo nitrogen are known, none coming within the scope of this invention.

H. Wieland et al., Ann. 514, 145 (1934).

D. Y. Curtin et al., J. Org. Chem. 21, 1221 (1956).

C. G. Overberger et al., J. Am. Chem. Soc. 80, 6562 (1958); ibid 81, 2154 (1959).

D. C. Iffland et al., J. Am. Chem. Soc. 83, 747 (1961).

M. C. Chaco et al., J. Org. Chem. 27, 2765 (1962).

Other known azo compounds include unsymmetrical azonitriles (U.S. Pat. Nos. 2,778,818 and 3,282,912; and Canadian Pat. No. 724,144).

To the best of applicants' knowledge, the alpha-amido and alpha-amidoximo azoalkanes of this invention have not been previously reported.

2,2'-Azobis (isobutyronitrile), commonly called AIBN, is a commercially available compound of the type disclosed by C. G. Overberger and co-workers and has the structure:

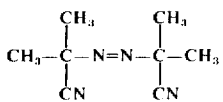

AIBN has many shortcomings. It is a toxic solid. Moreover, the decomposition residue, 2,2,3,3-tetramethylsuccinonitrile, is a highly toxic solid ($LD_{50}$=30 mg/kg in ratg — R. N. Harger et al., Federation Proceedings, 8205(1949)). Thus, it presents a toxic dusting problem when used in commercial operations and extreme precautions are required in its handling. It cannot be used as a blowing agent for the great majority of the plastic foam market due to the high levels of toxic residue left in the foamed product. It is insoluble in petroleum hydrocarbon solvents and possesses very low or limited solubility in most of the common organic solvents, especially those which are compatable with polymerization systems. This insoluble nature eliminates its use for many applications for which it would otherwise be suitable. It presents problems of metering, incorporation, mixing, dispersing, etc., and necessitates the use of a solvent that in many cases is not ideally suited for the particular application.

In general, the new compositions of the present invention eliminate these problems. The tertiary-(alkyl, cycloalkyl, bicycloalkyl or aralkyl) group on the one side of the azo function lowers the melting point of these compounds so that most of them are liquids or low melting solids which can be handled in the melted state. In addition, this tertiary group increases the solubility of these azos so that most of them are completely miscible with the common organic solvents including petroleum hydrocarbons. Thus, no dusting, metering, incorporating, mixing, and dispersing problems are encountered in using these new compositions. Also, the new compositions and their decomposition residues have chemical structures that suggest that they are, for the most part, significantly less toxic. Preliminary toxicological studies on the new compositions made in Examples I and II, set out later, indicate that they are significantly less toxic than AIBN. The less toxic nature of the new compositions coupled with their liquid and high solubility properties allows them to be used in many applications where AIBN cannot be used.

To the best of applicants' knowledge, none of the unsymmetrical alpha-cyano hydrazoalkanes of the subject invention have been previously reported, though the above-cited C. G. Overberger et al. and U.S. Pat. No. 2,778,818 disclose, respectively, symmetrical alpha, alpha'-dicyano-hydrazoalkanes and 2-(2'-hydroxyethyl-hydrazo)-2,4-dimethylvaleronitrile (primary alkyl group connected to the hydrazo group). Unsymmetrical t-carbon containing hydrazo compounds are reported by: Thiele, B. 28,2600; Angeli, Rome Atti Accad Tincei 26 I, 95 (1917); Thiele et al., Ann. 282,33 (1894); D. Neighbors et al., J. Am. Chem. Soc. 44, 1557 (1922).

Processes for preparing azonitriles have been reported by C. G. Overberger et al., J. Am. Chem. Soc. 71, 2661 (1949) and 80, 6562 (1958); Canadian Pat. Nos. 724,144 and 750,380; and U.S. Pat. Nos. 2,469,358; 2,778,818; and 3,282,912.

Since the subject compounds are novel, their use as initiators for vinyl polymerization, curing of resins, blowing agents, etc. have not been previously reported.

BRIEF SUMMARY OF THE INVENTION

The subject invention broadly pertains to:

1. Unsymmetrical tertiary-aliphatic azoalkanes containing one alpha-cyano group per azo group and their derivatives as represented by the formula

(1)

where $(R'')_3C-$ is a tertiary- (alkyl, cycloalkyl or aralkyl) radical where $R''$ is alkyl, aralkyl or aryl, not more than one $R''$ being aromatic; $R_1$ and $R_2$ are aliphatic or cycloaliphatic and together can form an alkylene diradical, and $R_2$ can also be phenol or substituted phenyl; and Z is —CN,

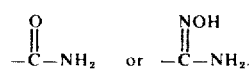

2. Unsymmetrical tertiary-aliphatic hydrazoalkanes (intermediates for I), of the formula

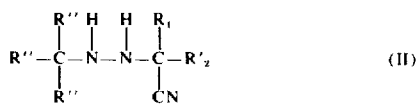 (II)

where R'' and R₁ are as defined in (1). R'₂ is the same as R₂ except that R'₂ can not be aryl.

3. Process for preparing compounds (I):

a. Reacting a hydrazine, $(R'')_3C—NH—NH_2$, with a ketone,

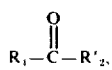

to form the hydrazone

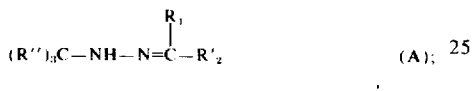 (A);

reacting (A) with hydrogen cyanide at a temperature of from about 0° to 80°C. (preferably 10°–80°C., most preferably at 10°–40°C.) to form the hydrazo

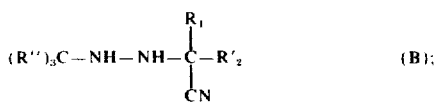 (B);

and oxidizing (B) to form the corresponding desired azo product

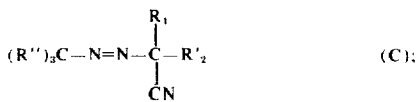 (C);

where R'', R₁ and R'₂ are as above defined.

b. Reacting a hydrazine, $(R'')_3C—NH—NH_2$ (preferably its acid salt $(R'')_3C—NH—\overset{HX}{} \cdot 2·HX$ where X is chlorine or bromine) with hydrogen cyanide or, preferably, an alkali metal cyanide (such as NaCN or KCN) and a ketone,

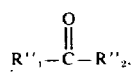

in water to form the hydrazo compound

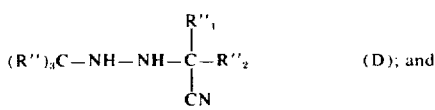 (D); and and oxidizing (D) to the corresponding desired azo product

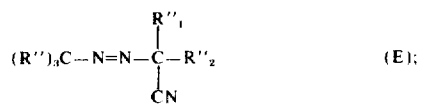 (E);

where R'' is as above defined; R''₁ is methyl or ethyl; R''₂ is unbranched lower alkyl of 1–6 carbons, 2-carboxyethyl or $(CH_2)_{1-3}OH$; and R''₁ and R''₂ taken together can form the diradical $—CH_2(CH_2)_nCH_2—$ where $n$ is 2–5 and the diradical can also be substituted with lower alkyl groups except on both terminal methylene groups or on either terminal methylene group when the substituent is particularly bulky such as t-butyl.

c. Reacting an alpha-haloazo compound

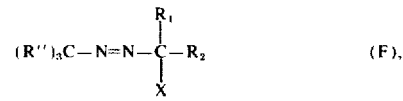 (F), where X is chlorine, bromine or iodine (preferably chlorine or bromine), with MCN (where M is alkali or alkaline earth metal, preferably Na, K, Cs, or Ag) to give the desired azo product

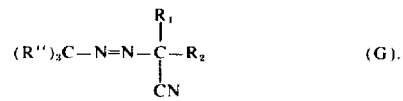 (G).

4. Improved processes for the preparation of polymers or copolymers from unsaturated monomers wherein the polymerization is carried out in the presence of an added free radical affording compound as the polymerization initiator (such as polymerizing vinyl monomers, curing unsaturated polyester resins, etc.), the improvement residing in the use of compounds (I) as the initiator.

DETAILED DESCRIPTION OF INVENTION

Azo Compounds

The azo compounds (I) are characterized by having a tertiary group, $(R'')_3C—$, attached to one of the azo nitrogens. This group increases the solubility of the azos relative to previously reported azobisnitriles in the common organic solvents, especially in hydrocarbon solvents which are the most desirable solvents for use in vinyl polymerizations. The $(R'')_3C—$ group also lowers the melting point of the compounds so that most of them are liquids or low melting solids and can be easily dispersed in monomers without requiring a solvent. Compared to the commercially available azobisnitriles, the $(R'')_3C—$ group lowers the toxicity of the (I) compounds and likewise reduces the toxicity of their decomposition residues. Being tertiary, this group has the important characteristic that the (I) compounds cannot tautomerize to hydrazones on heating or storage.

The definitions of R'', R₁ and R₂ are intentionally broad because their definition does not affect the general utility of the compounds nor the ability to prepare the compounds by the processes set forth herein as illustrated by the numerous examples. For practical reasons, however, the following preferred definitions can be given:

R" = lower alkyl of about 1–13 carbons (preferably 1–8 carbons, most preferably 1–8 carbons), aralkyl of 7–12 carbons (such as benzyl or phenethyl), or phenyl (can include one or more hydrocarbon substituents such as tolyl and xylyl so that the aryl group contains 6 to about 14 carbons), not more than one of the R" groups being aromatic. It is also contemplated that one or more of the R"s may be joined to form a cyclo, bicyclo or tricyclo radical of 3–12 carbons.

$R_1$ and $R_2$ = an alkyl or substituted alkyl of 1–20 carbons (the alkyl portion preferably containing 1–11 carbons, most preferably 1–6 carbons); cycloaliphatic having 1–2 condensed rings and optionally containing hydrocarbon substituents (preferably cycloalkyl or bicycloalkyl of 3–10 carbons, most preferably 3–7 carbons); or, taken together, an alkylene biradical of 2–16 carbons (preferably 3–11 carbons, most preferably 4–7 carbons); and $R_2$ can also be phenyl or substituted phenyl (preferably of 6–14 carbons). It is also contemplated that $R_1$ and $R_2$ may be a 5–6 membered heterocyclic radical. The preferred $R_1$ and $R_2$ substituents are (when Z is cyano, amido or amidoximo) lower (i.e., 1–4 carbons) alkoxy, phenoxy or alkyl substituted phenoxy, and (when Z is cyano or amido) carboxy, and (when Z is cyano) lower alkyl, hydroxy, alkoxycarbonyl, acyloxy, halogen, cyano or alkylsulfonato. The terms aliphatic and cycloaliphatic are used herein in their normal chemical meaning-the non-hydrocarbon substituents must not interfere with the preparation reactions.

The half-lives (an important criteria for utility) of the (I) compounds follow the general trend noted by Overberger et al. in the above-cited series of papers. The half-lives are dependent on R", $R_1$, $R_2$ and Z. The alpha-amido and alpha-amidoximo azos (I when Z is $-C(O)NH_2$ or $-C(NOH)NH_2$) are more stable then the corresponding cyano compounds. When R" and/or $R_2$ are aryl, the compounds are much less stable than the corresponding alkyl compounds and hence would be utilized in polymerizations at lower temperatures. Beta-branching in the $R_1$ and $R_2$ groups tend to destabilize (lower the stability of) the azos, the greater the beta-branching the greater the destabilization. Also, when $R_1$ and/or $R_2$ are cyclopropyl groups, the azo compounds are destabilized relative to the corresponding methyl compounds. These facts are illustrated further in the examples below where the 10 hour half-lives are given for many of the compounds. It is also reflected in the polyester cure times at various temperatures and the polystyrene initiating efficiencies at various temperatures in the examples.

Hydrazo Compounds

The hydrazo compounds (II) are defined above, the preferred definitions being the same as given above for compounds (I). They are intermediates in the preparation of the (I) azos. Their preparation is shown herein and in copending parent application Ser. No. 725,180.

Processes

The azo compounds (I) of this invention are easily prepared from hydrazines containing one of the defined tertiary groups, $(R")_3C-$, as shown in the examples. The t-alkylhydrazines were difficult to prepare prior to the teachings of parent patent application Ser. No. 409,306, filed 11/5/64 by C.S. Sheppard et al. of common assignee. The process described in Ser. No. 409,306 produces t-alkylhydrazines in a simple and economical manner and is suited for commercial production.

Three processes for preparing compounds coming within Formula I are described below:

Process (a)

This process prepares azo compounds (C) by adding hydrocyanic acid to a preformed hydrazone (A) of a ketone

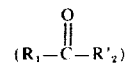

to form a hydrazo compound (B), and then oxidizing (B) to form the desired azo product (C).

The hydrazone (A) is preferably prepared in the presence of an inert solvent (such as benzene or like hydrocarbon) while removing the water produced substantially continuously during the reaction (such as by azeotroping off the water from a benzene solution). Alternatively, an alcohol solution of the hydrazine and ketone can be refluxed and the alcohol then evaporated. The reaction is carried out at a temperature which will facilitate the preferred removal of water.

The hydrazone (A) may be diluted with a nonreactive solvent such as a hydrocarbon, chlorinated hydrocarbon, ether or ester. While water may be present, the reaction with hydrogen cyanide runs better with as little water present as possible. The reaction can be run over a period of 1 hour to 1 week or longer, but usually about 3 hours at room temperature or above is sufficient. The reaction can be run in an autoclave, a pressure bottle, or in a reactor equipped with a condenser cold enough to condense HCN vapors back into the reaction medium. For optimum yields, a slight molar excess of HCN over the hydrazone is desired. After the reaction is complete, excess HCN can be removed with a vacuum or by washing with water. In some cases, it is desirable not to remove the excess HCN.

In the final step, the hydrazo compound (B) is oxidized under conventional conditions, such as by contacting it with an aqueous solution of alkali metal hypohalite or aqueous chlorine at temperatures near the freezing point of water, e.g., 0°–10°C. For hydrazos that readily evolve HCN in the presence of water, it is preferable to use non-aqueous oxidizing systems (such as mercuric oxide) or to add the hydrazo to an aqueous solution of the oxidizing agent at a rate and temperature such that the hydrazo compound will be readily oxidized to the stable azo compound before it can revert to the hydrazone. In some cases it is also advantageous to convert the hydrazo to its more stable acid salt (such as the hydrochloride) before oxidizing. Other oxidizing agents include: potassium permanganate, lead tetraacetate, ammonium nitrate, nitric acid, bromine, and the oxides of silver and mercury. Optionally, an organic solvent may also be present.

Process (b)

The concentration of the hydrazine or hydrazine salt reactant in the water may vary over a large range, i.e. from less than about 1% to greater than about 50%, but for practical use it is preferential to use a solution of about 5 to 20%. If a concentration of less than 5% is used, the yield decreases slightly and the amount of product obtained per reactor volume is small. On the other hand, if the concentration exceeds 20%, the hydrazine salt usually crystallizes out. If the free base is used, higher concentrations are practical. Hydrocyanic acid, NaCN, KCN or any other economical source of cyanide ion can be used, but the pH of the resulting aqueous solution must be adjusted to essentially neutral or slightly basic so as not to form water soluble acid salts of the hydrazo (D). The ketones suitable for use in this process are methyl or ethyl ketones of 3–9 carbons which are non-sterically hindered, non-sterically hindered cycloalkanones of 5 to 8 carbon atoms or non-sterically hindered, substituted cyclopentanones and cyclohexanones. Examples of suitable ketones are acetone, methyl ethyl ketone, 1-acetyl-3-propanol, hydroxyacetone, 2-octanone, levulinic acid, cyclohexanone, methyl n-propyl ketone, diethyl ketone, 2-methylcyclohexanone 3-methyl-cyclohexanone, 4-methylcyclohexanone, cyclopentanone, methyl benzyl ketone, ethyl acetoacetate, methyl acetoacetate and acetonyl acetate.

The reaction works very well with the lower molecular weight ketones such as acetone, methyl ethyl ketone and methyl propyl ketone. As the molecular weight increases, the yield generally decreases. The reaction also works very well with cyclohexanone, 2, 3, or 4-methylcyclohexanone and cyclopentanone. In the case of the hydroxy containing ketones such as hydroxyacetone and 1-acetyl-3-propanol, the hydrazo reaction works very well, but the hydroxyl group has to be blocked in the case of hydroxyacetone before oxidizing and the hydroxy should be blocked in the case of 1-acetyl-3-propanol before oxidation to obtain the maximum yield and purity. In the 1-acetyl-3-propanol case, the blocking group can be removed after oxidation, but in the hydroxyacetone case, it may not because the beta-hydroxy azo is unstable and readily decomposes. In the case of levulinic acid, the hydrazo is water soluble and must be separated out of the water either by extraction or by exceeding the solubility by using concentrated hydrazine solutions.

The hydrazo reactions can be run at from about 10° to about 80°C, but preferably are run at 20°–60°C for 1–3 hours. Running the reaction at a lower temperature or for shorter periods of time usually results in lower yields. Running at higher temperatures usually results in some decomposition of the hydrazo, again resulting in lower yields. Shorter reaction periods can usually be compensated for by higher temperatures and vice versa. The hydrazo products in most cases have very low water solubility and can be easily separated from the aqueous solution. Those having water solubility, such as those derived from ketones having hydroxyl or carboxylic subsituents, can be extracted with chlorinated hydrocarbons.

The hydrazo compound is then oxidized under conventional conditions to the corresponding azo compound. The oxidation may be carried out neat or in a nonoxidizable solvent such as ether, benzene, hydrocarbons or chlorinated hydrocarbons. Suitable oxidizing agents include aqueous solutions of alkali metal hypohalite, preferably sodium hypochlorite; aqueous hypochlorous acid, bromine, potassium permanganate, lead tetraacetate, ammonium nitrate, nitric acid, and the oxides of silver and mercury. For economic reasons, each of handling, and purity of the final product, it is preferable to use aqueous solutions of sodium hypochlorite in most cases. The oxidations may be carried out from 0°C to just below the decomposition temperature of the azo. For the more vigorous oxidations, such as aqueous hypochlorous acid, it is preferable to run the oxidations at the lower temperatures where the exotherm can be easily controlled. For the less vigorous oxidizing agents such as silver or mercuric oxide, it is preferable to run the oxidations at room temperature or slightly higher. When using aqueous sodium hypochlorite, it is preferable to carry out the oxidations at 25°–50°C, carefully controlling the exotherm with a cooling bath.

The oxidation may be carried out by adding the oxidizing agent to the hydrazo or vice versa. Sometimes it is preferable to add the hydrazo to the oxidizing agent and in other cases, the reverse is true. The azos may be purified by washing them with aqueous acid. The aqueous acid wash destroys any undesirable by-product.

Process (c)

The haloazo compound (F) can be prepared as taught in our parent application Ser. No. 725,180 by reacting the corresponding hydrazine and ketone, and then halogenating the hydrazone.

The reaction with MCN is carried out in a solvent system for the haloazo compound (F) and the metal cyanide, normally at from about 0° to about 50°C., preferably at 10°–30°C. If the reaction is run much below 10°C, the rate of reaction is quite slow and if the reaction is run much above 30°C, problems occur with the stability of the haloazo and may also cause problems with the stability of some of the products depending on their structure.

Suitable solvents for the reaction include the lower molecular weight alcohols ($C_1$–$C_5$ alcohols), ethers such as dioxane, glyme, and diglyme, dimethylformamide, acetone and methyl ethyl ketone. Preferably these solvents are mixed with water to give aqueous solutions which dissolve the metal cyanide more readily. Especially suitable solvents are 60–80% aqueous solutions of methanol, ethanol, dioxane, dimethylformamide or acetone. Since both water and alcohols react with the haloazos (see Ser. NO. 725,180), it is advisable to add the haloazo (F) to the cyanide solution (or slurry) so that an excess of cyanide is always present. Since the cyanide is more reactive toward the haloazos, only small amounts of the corresponding alpha-alkoxyazos and alpha-hydroxyazos will be formed. The small amounts of the alkoxyazos and hydroxyazos can be destroyed by washing the cyanoazos with acids such as hydrochloric or sulfuric acid diluted to about 10–20% with water. The alpha-haloazos can be added to the cyanide solution neat or in a non-reactive solvent (presumably the solvent it was made in), such as a hydrocarbon, chlorinted hydrocarbon, ether or low molecular weight ester such as ethyl acetate.

At the end of the reaction, the product can be isolated by diluting the reaction mixture with water to dissolve the salts and the water miscible solvent. The product or its solution will separate and can be purified by washing it with dilute solutions of acid and sodium bicarbonate.

Any metal cyanide can be used in the reaction, but for solubility and economic reasons sodium cyanide and potassium cyanide are the preferred reagents.

The alpha-cyanoazos (G) can be converted to the alpha-amidoazos

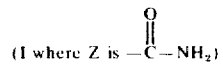

(I where Z is —C̈—NH$_2$)

by hydrolysis in concentrated sulfuric acid provided (G) does not contain any other hydrolyzable or acid sensitive groups. They can also be reacted with alcoholic solutions of hydroxylamine to form the corresponding alpha-amidoximoazos

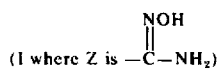

(I where Z is —C—NH$_2$)

provided R$_1$ and R$_2$ do not contain any substituents that will also react with alcoholic hydroxylamine. The amidoximoazos can also be acylated with acid chlorides or chloroformates using procedures well known in the art. The cyanoazos can also be hydrolyzed to esters and iminoesters with hydrogen chloride in anhydrous alcohol using procedures well known in the art.

Utility

These new compositions are free radical generators, polymerization initiators, curing agents for polyester resins, initiators for free radical initiated chemical reactions and blowing agents for producing foamed polymers and plastics.

These new compositions are initiators for the polymerization or copolymerization of unsaturated monomers such as alkenes, perfluoroalkenes, vinyl halides, vinyl esters, vinyl ketones, vinyl esters, vinylidene halides, alkenyl aromatics, allyl esters, allyl ethers and allyl ketones.

Illustrative polymerizable monomers are ethylene, vinyl chloride, vinylidene fluoride, vinylidene chloride, vinyl acetate, vinylpyridine, vinylpyrrolidone, vinylcarbazole, butadiene, isoprene, acrylonitrile, acrylic acid, acrylic acid esters, methacrylic acid, methacrylic acid esters, styrene, chlorostyrene, methylstyrenes, diallyl phthalate, allyl diglycol carbonate, perfluoropropene and tetrafluoroethylene. These new compositions are especially useful in the polymerization and/or copolymerization of ethylene, vinyl acetate, acrylonitrile, vinyl chloride, ethyl acrylate, methyl methacrylate and styrene.

These compositions are very efficient in the curing of polyester resins in the temperature range of 50° to 145°C depending on the half-life of the particular azo compound. The unpolymerized resins containing the azo compounds have very good pot-life (i.e., the length of time the resin may be left at ambient temperature with the curing agent mixed in it without the resin curing) in comparison to peroxide (having the same half-life) curing systems. The cure time of the resin is not effected by small amounts of impurities such as metal ions when these new azo compositions are used as the curing agents. This is not true when peroxide curing agents are used.

The novel I compounds evolve one mole of nitrogen gas per azo group in the compound when they are decomposed. In addition, other gasses are evolved from the breakdown and/or disproportionation of the radicals formed. Thus, the novel I compounds are useful in applications where copious quantities of gases are desired such as in producing foamed polymers.

In addition to the numerous examples to follow, the following compounds are also representative of compounds I and derivatives thereof.

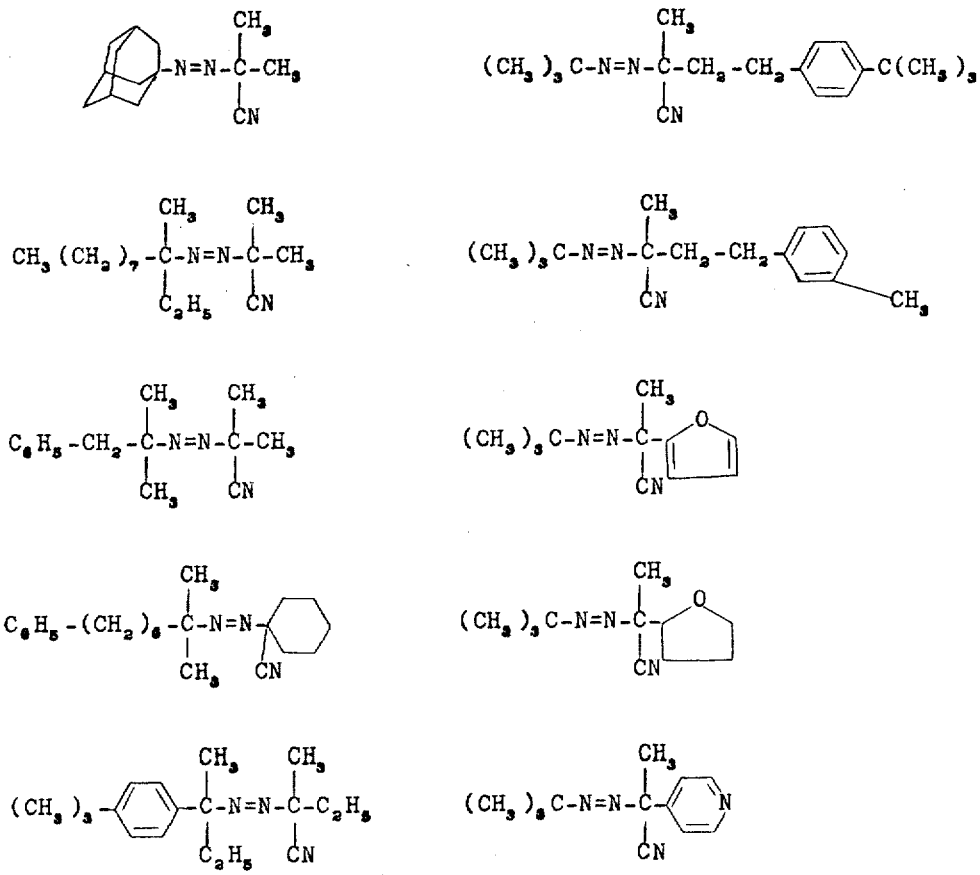

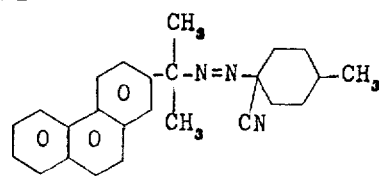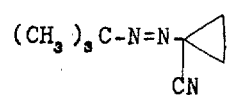
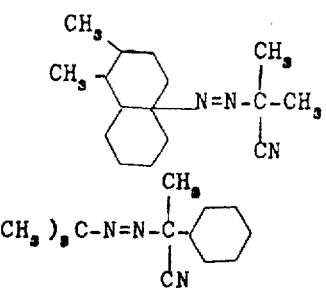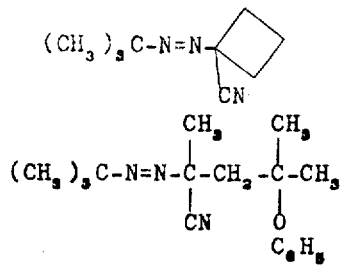
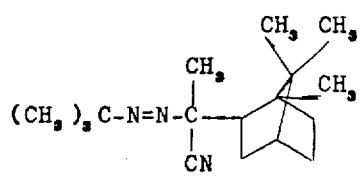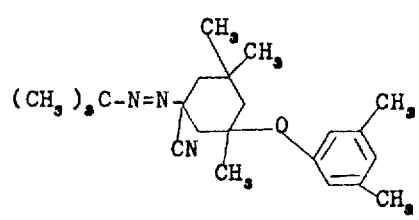
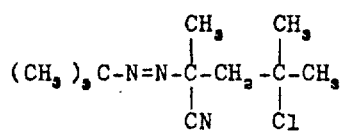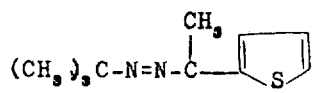
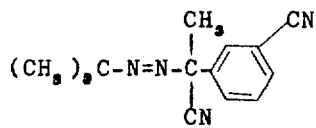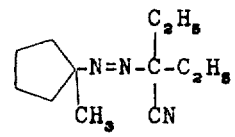
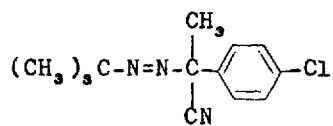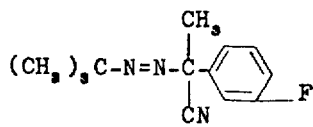
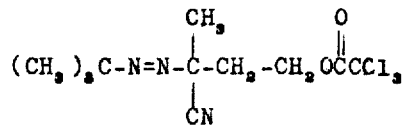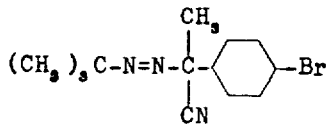
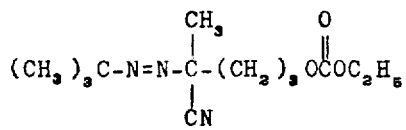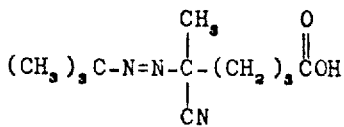
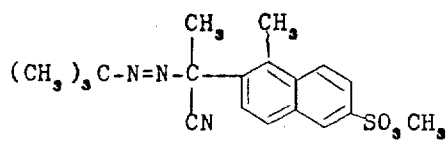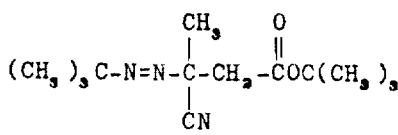

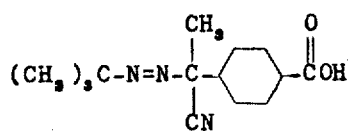
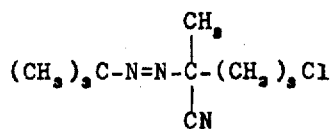
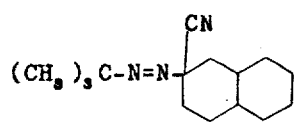
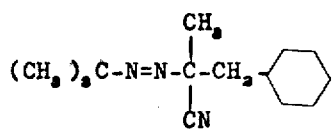
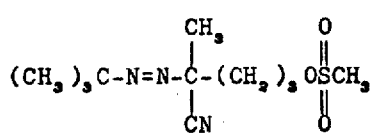
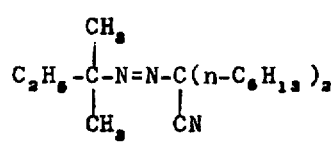
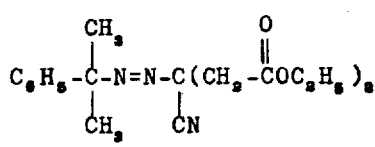
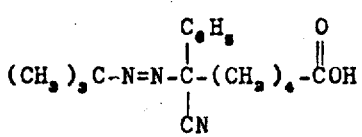
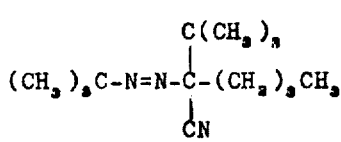
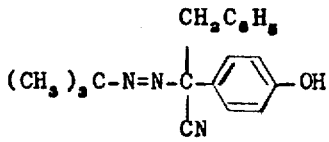
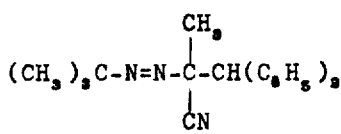
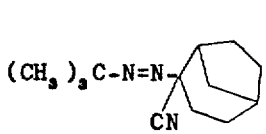
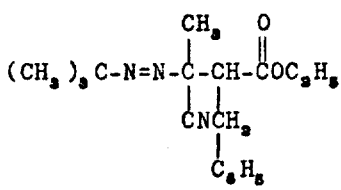
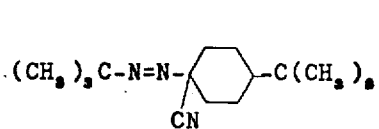
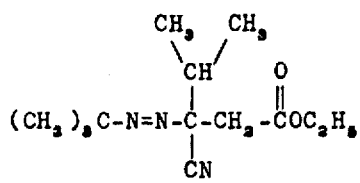
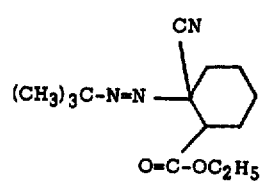
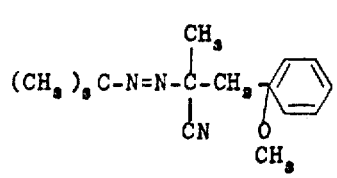
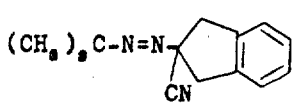
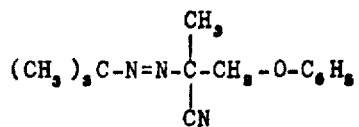
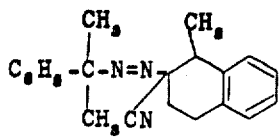

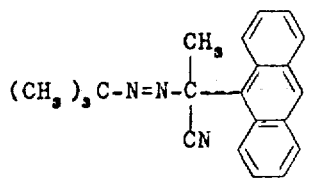 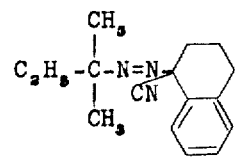
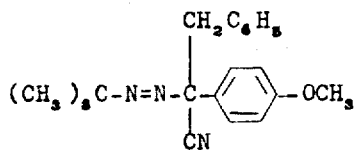 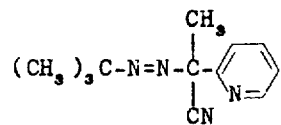
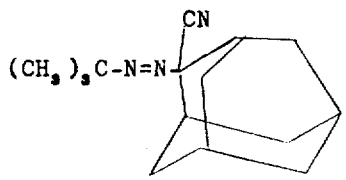 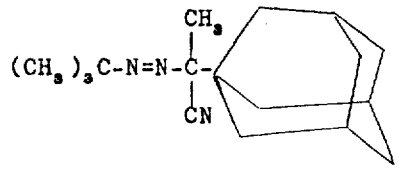
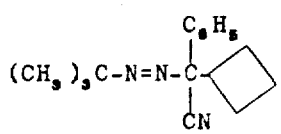 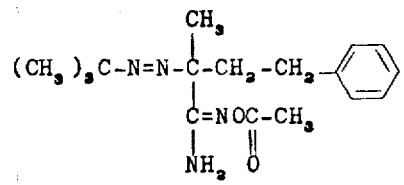
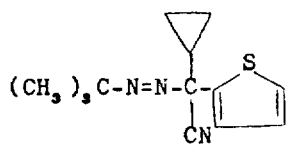 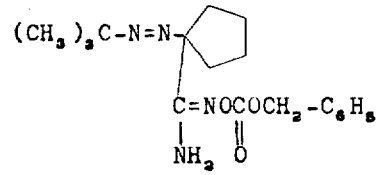
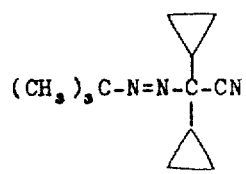 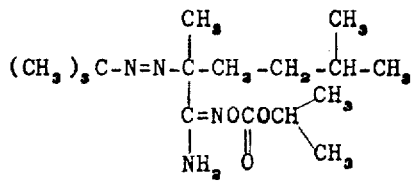
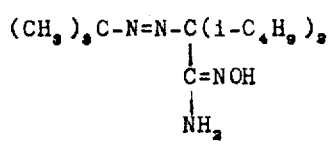 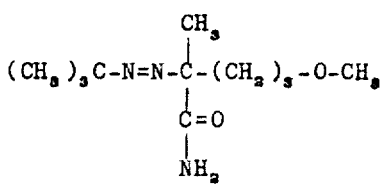
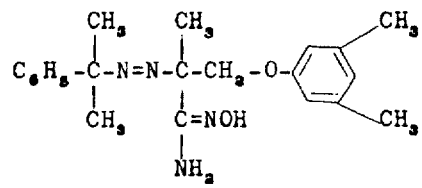 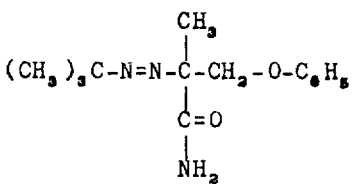

17 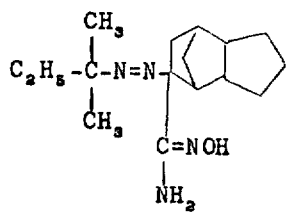 18 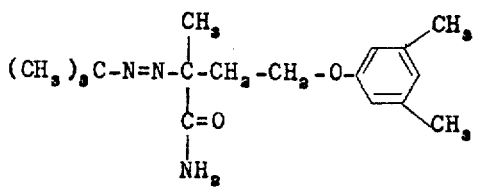

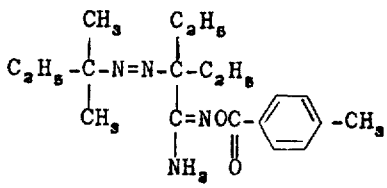 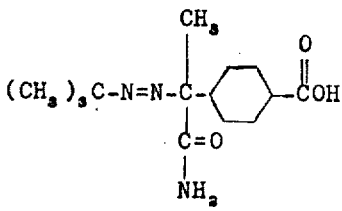

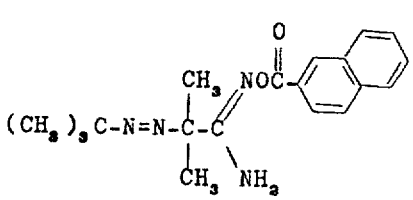 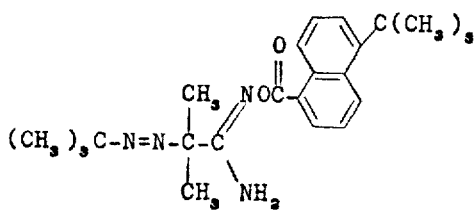

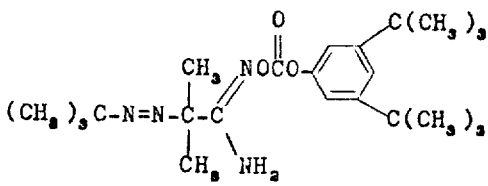

EXAMPLES

The following examples illustrate the subject compounds, processes and utility, but are not in limitation thereof.

EXAMPLE I

Preparation of 2-t-Butylazo-2-cyanopropane

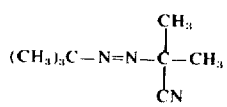

A. (1) Preparation of 2-t-Butylhydrazo-2-cyanopropane

To a stirred solution of 35.2 grams (0.28 moles) of t-butylhydrazine hydrochloride and 13.7 grams (0.28 moles) of sodium cyanide in 100 ml. of deionized water in a 200 ml. round bottom flask, was added 16.3 grams (0.28 moles) of acetone. The flask was stoppered and the reaction stirred overnight. The next morning the organic layer was separated, the aqueous layer extracted with 50 ml. of methylene chloride, and the methylene chloride layer and organic layer combined and dried over anhydrous sodium sulfate. The methylene chloride solution was filtered and the methylene chloride evaporated on a rotating evaporator. The yield was 42.1 grams (96.7%). The infrared spectrum contained strong NH bands, a cyano band, and did not contain any carbonyl or imino bands. Thus the infrared spectrum was consistent with the structure of the desired hydrazo product.

A. (2) Preparation of 2-t-Butylazo-2-cyanopropane

To 8.4 grams (.054 moles) of 2-t-butylhydrazo-2-cyanopropane in a 4 neck 250 ml. round bottom flask was added, with stirring, dropwise 100 ml. of a solution containing .054 moles of sodium hypochlorite (prepared from 3.85 grams of chlorine and 4.5 grams of sodium hydroxide in water), holding the temperature below 5°C. with an ice bath. The reaction was stirred an additional twenty minutes after the addition was over and the organic layer separated. The organic layer was washed with 10 ml. of 5% HCl, two 10 ml. portions of saturated NaHCO₃ solution, 10 ml. of deionized water, dried over anhydrous sodium sulfate and the product filtered. The yield was 6.0 grams (72.5%). The infrared spectrum did not contain any NH bands and was consistent with the structure of the proposed azo product. The material assayed 99.6% by gas chromatographic analysis. It is a liquid and is soluble in petroleum solvents. The following half-life data in trichlorobenzene have been determined:

| Temp. (°C.) | t½ (hours) |
|---|---|
| 70 | 40.5 |
| 78.8 | 10.0 |
| 90 | 2.0 |
| 100 | 0.54 |
| 110 | 0.20 |

B. (1) Preparation of 2-t-Butylhydrazo-2-cyanopropane

To a stirred solution of 62.4 grams (0.50 moles) of t-butylhydrazine hydrochloride and 25.8 grams (0.525 moles) of sodium cyanide in 450 ml of water in a 1½ liter jacketed resin reactor, equipped with a thermometer, mechanical stirrer, condenser and dropping funnel was added 29 grams (0.5 moles) of acetone. The reaction mixture exothermed to about 35°C. The reaction was then warmed to 40°C by circulating warm water through the jacket. The reaction was stirred 1 hour at 40°C, the aqueous layer seprated into 10% sodium hydroxide and set aside in the hood for detoxicafication by sodium hypochlorite solution. The organic layer was carefully transferred to a dropping funnel and the dropping funnel placed in the reactor head. A small sample of hydrazo was removed, dried over anhydrous Na₂SO₄ and its infrared spectrum run. The infrared spectrum contained strong NH bands, a cyano band and did not contain any carbonyl or imino bands. Thus, the infrared spectrum was consistent with the hydrazo structure.

B. (2) Preparation of 2-t-Butylazo-2-cyanopropane

To the resin reactor was added 450 ml of 11% (by weight) sodium hypochlorite solution. With rapid stirring, the 2-t-butylhydrazo-2-cyanopropane in the dropping funnel was slowly added, holding the reaction temperature at 25°-35°C by circulating cold water through the reactor jacket. The addition was carried out in one-half hour and the reaction mixture was stirred an additional one-half hour. (The oxidation was monitored by gas chromatography on a silicone grease column at 88°C). The aqueous layer was separated and the organic layer cooled to 10°C and washed with 50 ml of 10% HCl until the gassing ceased. The organic layer was then washed with 20% HCl, water, 10% NaHCO₃, dried, filtered and stripped on a rotating evaporator until the chloroform (a side product) was removed. The yield was 53.5 grams (70% yield) of 2-t-butylazo-2-cyanopropane. The infrared spectrum did not contain any N—H bands and was consistent with the structure of the proposed product. The material assayed 98.8% by gas chromatographic analysis, using a sample that had been purified by fractional distillation at reduced pressure as the analytical standard. The product is a liquid at room temperature, has a freezing point of 17°C and is very soluble in petroleum solvents.

2-t-Butylazo-2-cyanopropane is a thermally sensitive free radical and gas generator. It produces 179cc of gas per gram at 110°C. The compound has a 10 hour half-live in trichlorobenzene at 79°C and in odorless mineral spirits, it has a 10 hour half-life at 86°C.

EXAMPLE II

Polymerization of Styrene with 2-t-Butylazo-2-cyanopropane

Low Conversion

A solution of styrene containing $5\times10^{-4}$ moles per deciliter of 2-t-butylazo-2-cyanopropane was heated at 85°C and the change in density, which is a measure of polymer formation, was followed by means of a dilatometer to measure polymerization rates at 5% and 10% conversion to polystyrene. The rates obtained at 5% and 10% conversion were $9.73\times10^{-3}$ and $9.22\times10^{-3}$ moles per liter per minute respectively. Without the 2-t-butylazo-2-cyanopropane, the 5 and 10% rates were $0.92\times10^{-3}$ moles per liter per minute.

High Conversion

A series of pyrex test tubes was filled with styrene solutions containing varying amounts of 2-t-butylazo-2-cyanopropane. The amounts of azo initiator in the tubes were adjusted so that the resulting conversion versus concentration plots would cross 90% conversion, ideally, after 6.45 hours at 85°C. (The conversion figure was selected since styrene polymerizations are carried out almost to complete conversion commercially. Hence, initiators that dead-end before 90% conversion or achieve 90% conversion only after using very large quantities of initiator are not attractive commercially.) After flushing out the tubes with nitrogen gas, they were sealed and placed in a constant temperature bath thermostatted at 85°C. After 8.5 hours at 85°C., the tubes were removed and quickly chilled to 0°C to prevent post polymerization. The sealed tubes were then broken and the polymer dissolved in 1000 ml of methanol to precipitate the polystyrene. The polymer was separated by filtration and dried in an oven at 50°-55°C. The conversion of styrene to polymer was determined and plots of initiator concentration versus conversion were constructed. The initiator concentration required to attain 90% conversion was compared under similar conditions, to that of benzoyl peroxide. Equation (1) was used to determine efficiency data.

$$F_1/F_2 = Rp_1{}^2/Rp_2{}^2 \times Kd_2/Kd_1 \times [I]_2/[I]_1 \quad (1)$$

$F_1/F_2$ is the efficiency of 2-t-butylazo-2-cyanopropane compared to that of benzoyl peroxide ($F_2$). $Rp_1$ and $Rp_2$ are the rates of polymerization of the azo initiator and benzoyl peroxide, respectively, and $[I]_1$ and $[I]_2$ are concentrations of azo initiators and benzoyl peroxide, respectively, required for attainment of 90% conversion after 6.45 hours at 85°C. Under these conditions:

$$Rp_1{}^2/Rp_2{}^2 = 1$$

$Kd_2/Kd_1$ are also known from the half-lives of benzoyl peroxide and the azo initiator, respectively. Hence, the value of $F_1/F_2$ can be calculated and in the case of 2-t-butylazo-2-cyanopropane, $F_1/F_2$ was determined to be 1.10, therefore 2-t-butylazo-2-cyanopropane is a very efficient initiator for styrene polymerizations at 85°C.

EXAMPLE III

Curing an Unsaturated Polyester-Styrene Resin with 2-t-Butylazo-2-cyanopropane

An unsaturated polyester resin was made by reacting maleic anhydride (1.0 mole), phthalic anhydride (1.0 mole), and propylene glycol (2.2 moles) until an acid number of 45–50 was obtained. To this was added hydroquinone at a 0.013% concentration. Seven parts of this unsaturated polyester was diluted with 3 parts of monomeric styrene to obtain a homogeneous blend having a viscosity of 13.08 poise and a specific gravity of 1.14.

To 20 grams of this blend was added 0.128 gram of 2-t-butylazo-2-cyanopropane and the resultant composition placed in a constant temperature bath at 180°F (82°C). The internal temperature was recorded as a function of time and a peak exotherm of 381°F (194°C) was reached in 13.3 minutes indicating an excellent cure of the unsaturated polyester-styrene blend had occurred. The resultant cured material was very hard.

Without an initiator, no cure of this resin blend occurred after more than 30 minutes at 212°F (100°C).

EXAMPLE IV

Polymerization of Ethylene with 2-t-Butylazo-2-cyanopropane

Ethylene (99.5% minimum purity) was polymerized to polyethylene using 2-t-butylazo-2-cyanopropane as the polymerization initiator at 20,000 PSI reaction pressure and at temperatures of 375°F and also at 432°F. The polymerization was conducted in a one-liter stirred autoclave-type reactor wherein the fresh reactants were added continuously and the polyethylene and unreacted materials were continuously withdrawn. The initiator was diluted to 0.25 percent in odorless mineral spirits and this initiator solution was pumped directly to the reactor through a separate entry. A low molecular weight saturated hydrocarbon was added to the ethylene feed stream as a chain transfer agent. Its purpose was to increase melt index of the polyethylene produced so that product lines would not become plugged with low melt index (high molecular weight) polymer. The polyethylene and unreacted materials were withdrawn from the reactor to a separator where unreacted gases were rented through a pressure control valve. The molten polymer from the bottom of the separator was transferred into another vessel where additional unreacted gas was vented and the polyethylene continually withdrawn.

The results are summarized below and compared to an industry standard initiator, i.e. t-butyl peroxypivalate.

| Initiator | 2-t-butylazo-2-cyanopropane | | t-butyl peroxypivalate |
|---|---|---|---|
| Reaction Temperature, °F | 375 | 432 | 375 |
| Reactor Feed Temperature, °F | 140 | 108 | 163 |
| Reaction Pressure, PSI | 20,000 | 20,000 | 20,000 |
| Residence Time, sec. | 33 | 41 | 45 |
| Ethylene Conversion, % | 4.7 | 7.4 | 5.7 |
| Initiator efficiency, lbs. polymer/lb initiator | 2,630 | 1,440 | 460 |
| Melt index, g/10 min, of polyethylene | 3.98 | 9.36 | 3.07 |
| Density, g/cm³, of polyethylene | 0.9279 | 0.9219 | 0.9266 |
| Infra-red Results on Polyethylene: | | | |
| a) trans-internal unsaturation per 1000 carbons | 0.01 | 0.01 | 0.01 |
| b) terminal vinyls per 1000 carbons | 0.01 | 0.01 | <0.01 |
| c) Vinylidene groups per 1000 carbons | 0.12 | 0.19 | 0.14 |
| d) methyl to methylene ratio | 0.98 | 1.06 | 0.96 |

These results show that 2-t-butylazo-2-cyanopropane is a very efficient initiator for ethylene polymerization and produces polyethylene of at least equal quality to that produced by the presently used initiators in the industry.

EXAMPLE V

Preparation of 1-t-Butylazo-1-cyanocyclohexane

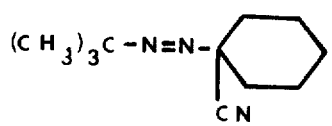

A. (1) 1-t-Butylhydrazo-1-cyanocyclohexane

To a rapidly stirred solution of 24.8 grams (0.2 mole) of t-butylhydrazine hydrochloride and 9.8 grams (0.2 mole) of sodium cyanide in 100 ml. of deionized water in a 250 ml. 4-neck round bottom flask, was added a solution of 19.6 grams (0.2 mole) of cyclohexanone in 15 ml. of ethanol. The reaction was stirred for 5 hours at room temperature and then allowed to stand overnight. The next morning the reaction was stirred an additional hour and filtered. The product was dried at 30°C. in a vacuum oven and the yield was 36.3 grams (93.5%) of a white solid melting at 70°–73°C. The white solid evolves HCN on exposure to air over extended periods. The infrared spectrum contained strong NH bands, a cyano band, and did not contain any carbonyl or imino bands. The infrared spectrum was thus consistent with the structure of the desired hydrazo product.

A. (2) 1-t-Butylazo-1-cyanocyclohexane

To a rapidly stirred mixture of 39.0 grams (0.2 mole) of 1-t-butylhydrazo-1-cyanocyclohexane, 200 ml. of methylene chloride and 100 ml. of water, was added 14.3 grams (0.2 mole) of chlorine at such a rate that the reaction temperature did not exceed 5°C. The reaction was stirred an additional 15 minutes after the addition was complete. The methylene chloride layer was separated, washed twice with 50 ml. portions of saturated $NaHCO_3$ solution, dried over anhydrous sodium sulfate, filtered, and the methylene chloride evaporated on a rotating evaporator to obtain 35.0 grams of liquid product that assayed 86.5% by an ultraviolet spectrophotometric analysis. Distillation gave a product, b.p. 71°C./1.2 mm. of Hg, that assayed 97.6% as 1-t-butylazo-1-cyanocyclohexane. The infrared spectrum was in accord with this structure. The following half-life data in trichlorobenzene have been determined:

| Temp. (°C.) | t ½ (hours) |
|---|---|
| 96.3 | 10.0 |
| 100 | 6.7 |
| 110 | 2.3 |
| 120 | 0.75 |

B. (1) 1-t-Butylhydrazo-1-cyanocyclohexane

To a rapidly stirred solution of 62.4 grams (0.50 moles) of t-butylhydrazine hydrochloride and 25.8 grams (0.525 moles) of sodium cyanide in 450 ml of water in a 1½ liter jacketed resin reactor equipped with a thermometer, mechanical stirrer, condenser and dropping funnel was added 49 grams (0.5 moles) of cyclohexanone. The reaction mixture exothermed to about 35°C. The reaction was then warmed to 45°–50°C by circulating hot water through the jacket. The reaction was stirred 1½ hours at 45°–50°C and then 100 ml of hexane was added to dissolve the solid hydrazo. The temperature had to be kept at 40°C or above to completely dissolve the hydrazo in the hexane. The aqueous layer was separated into 10% sodium hydroxide and set aside in the hood for detoxicafication by sodium hypochlorite solution. The hexane solution was washed with 400 ml of warm water and the wash separated at 40°C or above. A small sample of the hexane solution was dried, the hexane evaporated and an infrared spectrum run on the resultant solid. The infrared spectrum contained strong NH bands and a cyano band and did not contain any carbonyl or imino bands. Thus, the infrared spectrum was consistent with the structure of the desired product.

B.(2)1-t-Butylazo-1-cyanocyclohexane

To the rapidly stirred solution of 1-t-butylhydrazo-1-cyanocyclohexane in the jacketed reactor was added 450 ml of 11% (by weight) sodium hypochlorite solution over 1 hour. The reaction mixture was warmed to 40°–45°C at the beginning of the addition and then the temperature held at 40°–50°C throughout the hypochlorite addition by periodically circulating cold or hot water through the reactor jacket, whichever was necessary to hold the temperature in the desired temperature range. After the addition was over, the reaction mixture was stirred at 40°–50°C until gas chromatography (one-half meter silicone grease column at 120°C) indicated the oxidation was complete (usually about 15 minutes). The reaction mixture was cooled to room temperature, the aqueous layer separated and the organic layer successively washed with water, 10% HCl, 20% HCl, water, 10% $NaHCO_3$, dried over anhydrous $Na_2SO_4$, filtered and the hexane evaporated on a rotating evaporator to leave 82.3 grams (85% yield) of a light yellow liquid. Upon standing at room temperature, the liquid slowly crystallized. The infrared spectrum did not contain any N-H bands and was consistent with the structure of 1-t-butylazo-1-cyanocyclohexane. The product assayed 97.7% by gas chromatographic analysis. The gas chromatography standard of 1-t-butylazo-1-cyanocyclohexane was purified by distillation (b.p. 71°C at 1.2 mm of Hg) followed by low temperature recrystallization from pentane.

1-t-butylazo-1-cyanocyclohexane is a thermally sensitive free radical and gas generator. It produces 146cc of gas per gram at 130°C. The compound has a half-life of 10 hours at 96°C in trichlorobenzene.

The styrene polymerization rates at 5% and 10% conversion for 1-t-butylazo-1-cyanocyclohexane at 85°C were $3.68 \times 10^{-3}$ and $3.33 \times 10^{-3}$ moles per liter per minute respectively and at 100°C they were $13.3 \times 10^{-3}$ moles per liter per minute. Without the 1-t-butylazo-1-cyanocyclohexane, the 5% and 10% rates at 100°C were $2.81 \times 10^{-3}$ moles per liter per minute. The method described in Example II was used.

Using the procedure described in Example III, 0.2 grams of 1-t-butylazo-1-cyanocyclohexane cured 20 grams of the unsaturated polyester-styrene resin in 10 minutes giving a peak exotherm of 414°F (212°C). The resultant cured piece was very hard.

EXAMPLE VI

Preparation of 2-t-Butylazo-2-cyanobutane

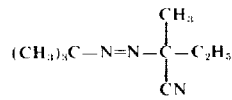

A. Preparation of 2-t-Butylhydrazo-2-cyanobutane

To a stirred solution of 62.4 grams (0.50 moles) of t-butylhydrazine hydrochloride and 25.8 grams (0.525 moles) of sodium cyanide in 450 ml of water in a 1½ liter jacketed resin reactor, equipped wtih a thermometer, mechanical stirrer, condenser and dropping funnel was added 36.1 grams (0.5 moles) of methyl ethyl ketone. The reaction mixture exothermed to about 35°C. The reaction was then warmed to 40°C by circulating warm water through the jacket. The reaction was stirred 1 hour at 40°C, the aqueous layer separated into 10% sodium hydroxide and set aside in the hood for detoxicafication by sodium hypochlorite solution. The organic layer was carefully transferred to a dropping funnel and the dropping funnel placed in the reactor head. A small sample of the hydrazo was removed, dried over anhydrous $Na_2SO_4$ and its infrared spectrum run. The infrared spectrum contained strong NH bands, a cyano band and did not contain any carbonyl or imino bands. Thus, the infrared spectrum was consistent with the hydrazo structure.

B. Preparation of 2-t-Butylazo-2-cyanobutane

To the resin reactor was added 450 ml of 11% (by weight) sodium hypochlorite solution. With rapid stirring the 2-t-butylhydrazo-2-cyanopropane in the dropping funnel was slowly added, holding the reaction temperature at 25°–35°C by circulating cold water through the reactor jacket. The addition was carried out in one-half hour and the reaction mixture was stirred an additional one-half hour. (The oxidation was monitored by gas chromatography on a silicone grease column at 90°C). The aqueous layer was separated and the organic layer cooled to 10°C and washed with 50 ml of 10% HCl until the gassing ceased. The organic layer was then washed with 20% HCl, water, 10% NaHCO$_3$, dried, filtered and stripped on a rotating evaporator until the chloroform (a side product) was removed. The yield was 54.5 grams (65% yield) of 2-t-butylazo-2-cyanobutane. The infrared spectrum did not contain any N-H bands and was consistent with the structure of the proposed product. The material assayed 98% by gas chromatographic analysis, using a sample that had been purified by fractional distillation at reduced pressure as the analytical standard. The product is a liquid at room temperature and has a freezing point of −25°C. It is very soluble in hydrocarbon solvents even at temperatures as low as −20°C.

The compound has a 10 hour half-life in trichlorobenzene around 80°C and around 82°C in odorless mineral spirits. The styrene polymerization rates at 5 and 10% conversion for 2-t-butylazo-2-cyanobutane at 85°C were 8.45 × 10$^{-3}$ moles per liter per minute and 8.04 × 10$^{-3}$ moles per liter per minute respectively using the method described for low conversion polymerization in Example II. In the high conversion polymerization of styrene using the procedure described in Example II, F$_1$/F$_2$ = 0.81 at 85°C where F$_1$ is 2-t-butylazo-2-cyanobutane and F$_2$ is benzoyl peroxide. Using the procedure described in Example III, 0.2 grams of 2-t-butylazo-2-cyanobutane cured 20 grams of the unsaturated polyester-styrene resin at 212°F (100°C) in 3.2 minutes giving a peak exotherm of 420°F (216°C). The resultant cured piece was very hard.

EXAMPLE VII

Preparation of
4-t-Butylazo-4-cyano-2,6-dimethylheptane

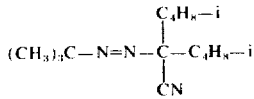

A. t-Butylhydrazone of diisobutyl ketone

The t-butylhydrazone of diisobutylketone was prepared in 94.5% yield by heating a solution of 5.0g. (0.057m) t-butylhydrazine, 8.1g. (0.057m) diisobutylketone and 0.1g. p-toluene-sulfonic acid in benzene and azeotroping off the water formed in the reaction. The reaction was refluxed 4 hours and the benzene evaporated off on a rotating evaporator. The liquid product weighed 11.45g. (94.5%) and the infrared spectrum was consistent with the proposed structure.

B. 4-t-Butylhydrazo-4-cyano-2,6-dimethylheptane 4-t-Butylhydrazo-4-cyano-2,6-dimethylheptane was prepared in 99% yield by heating a solution of 11.0g. of diisobutylketone t-butylhydrazone in 20 ml. of liquid HCN at 50°C for 6 hours. The excess HCN was evaporated off into a dry ice trap leaving 12.1g. (99%) of the liquid product. The infrared spectrum was consistent with the proposed structure of the compound (strong NH and weak CN bands).

C. 4-t-Butylazo-4-cyano-2,6-dimethylheptane

To a rapidly stirred mixture of 12.1g. (0.046 m.) of 4-t-butylhydrazo-4-cyano-2,6-dimethylheptane, 30 ml. methylene chloride and 15 ml. water was added 7.35g. (0.046 m.) bromine at such a rate that the reaction temperature did not exceed 5°C. The reaction was stirred an additional 15 minutes after the addition was complete. The methylene chloride layer was separated, washed twice with 50 ml. portions of saturated NaHCO$_3$ solution, dried over anhydrous sodium sulfate, filtered, and the methylene chloride evaporated on a rotating evaporator to obtain 11.5 grams of liquid product. The infrared spectrum was in accord with the structure of 4-t-butylazo-4-cyano-2,6-dimethylheptane.

4-t-butylazo-4-cyano-2,6-dimethylheptane is a thermally sensitive free radical and gas generator. It has a 10 hour half-life in trichlorobenzene at 61°C. At a 1.0 weight percent loading it cured the unsaturated polyester-styrene resin of Example III at 180°F. (82.2°C.) giving a peak exotherm of 371°F in 2.8 minutes and a very hard cured resin.

EXAMPLE VIII

Preparation of
1-t-Butylazo-1-cyano-3,3,5-trimethylcyclohexane

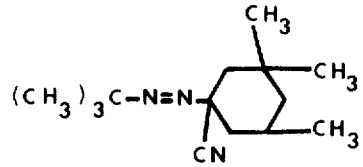

A. t-Butylhydrazone of Dihydroisophorone

The same procedure as was used in Example VIIA was used for the preparation of dihydroisophorone t-butylhydrazone. The yield of liquid product was 12.0 grams (100% yield) and the infrared spectrum was consistent with the structure of the proposed compound.

B. 1-t-Butylhydrazo-1-cyano-3,3,5-trimethylcyclohexane 1-t-Butylhydrazo-3,3,5-trimethylcyclohexane was prepared in the same manner as 4-t-butylhydrazo-4-cyano-2,6-dimethylheptane in Example VIIB. The liquid product was used directly in the next step.

C. 1-t-Butylazo-1-cyano-3,3,5-trimethylcyclohexane 1-t-Butylazo-1-cyano-3,3,5-trimethylcyclohexane was prepared by bromine oxidation of the above 1-t-butylhydrazo-1-cyano-3,3,5-trimethylcyclohexane in the same way that 4-t-butylhydrazo-4-cyano-2,6-dimethylheptane was oxidized in Example VIIC. The yield of liquid product was 8.2 g. (63%) and the infrared spectrum was consistent with the structure of the proposed compound.

1-t-butylazo-1-cyano-3,3,5-trimethylcyclohexane is a thermally sensitive free radical and gas generator. It has a 10 hour half-life in trichlorobenzene at 78°C. At a 1.0 weight percent loading it cured the unsaturated polyesterstyrene resin of Example III at 180°F. (82.2°C.) giving a peak exotherm of 384°F (195.6°C.) in 9.4 minutes and a very hard cured resin.

EXAMPLE IX

Preparation of
2-t-Butylazo-2-cyano-3,3-dimethylbutane

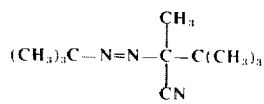

A. Pinacolone t-Butylhydrazone

To a solution of 5g. (0.05 m.) pinacolone in 50 ml benzene was added 5 g. (0.057 m.) t-butylhydrazine and a spatula tip of para-toluenesulfonic acid. The flask was fitted with a Dean Stark trap and the reaction refluxed until 0.9 ml. (0.05 m.) of water was azeotroped off. The solution was cooled down and the benzene stripped off leaving 8.5g (100%) of a white fluffy solid. The infrared spectrum of the solid was consistent with the structure of the proposed compound.

B. 2-t-Butylhydrazo-2-cyano-3,3-dimethylbutane

To a solution of 7.0g (0.0413 m.) of pinacolone t-butylhydrazone in 20 ml of benzene in a pressure bottle was added 20 ml of liquid HCN. The bottle was stoppered and the reaction heated at 50°C for 4 hours. The reaction cooled down and the benzene and HCN stripped off. The yield was 8.0g of a crude solid. The solid was dissolved in pentane, the pentane solution dried over anhydrous sodium sulfate, filtered, and the pentane stripped off. The yield was 7.7g (94%) of a tan solid, melting range 67°–74°C. The infrared spectrum was consistent with the structure of the proposed product.

C. 2-t-Butylazo-2-cyano-3,3-dimethylbutane

To a mixture of 7.7g (0.039 m.) 2-t-butylhydrazo-2-cyano-3,3-dimethylbutane, 50 ml. methylene chloride and 25 ml water, cooled to 0° in an ice bath, was added 6.25g (0.039 m.) bromine dropwise over 15 minutes holding the temperature at 0° to 5°C. After the bromine addition, the reaction was stirred 10 minutes, the methylene chloride layer separated, washed twice with 10% NaHCO₃ solution, dried over anhydrous sodium sulfate, filtered and the methylene chloride evaporated off. The yield was 7.6g (100%) of a white solid with a melting range of 38°–40°C. Its infrared curve was in accord with the structure of 2-t-butylazo-2-cyano-3,3-dimethylbutane. The product is a thermally sensitive free radical and gas generating compound. It has a 10 hour half-life in trichlorobenzene at 80°C.

It cured the unsaturated polyester-styrene resin of Example III at 180°F (82.2°C) and 212°F (100°C) giving peak exotherms of 388°F (197.8°C) and 430°F (221.1°C) in 10.4 and 4.9 minutes respectively. The cured samples were very hard.

EXAMPLE X

Preparation of 4-t-Butylazo-4-cyanovaleric Acid

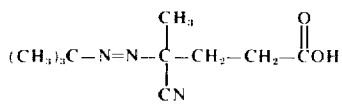

To a solution of 312 grams (2.5 moles) of t-butylhydrazine hydrochloride in 800 mls of water in a 3 liter jacketed resin reactor equipped with an efficient mechanical stirrer, thermometer, condenser and dropping funnel was added 123 grams (2.5 moles) of sodium cyanide and 290 grams (2.5 moles) of levulinic acid from the dropping funnel over 5 minutes. The reaction exotherms to 40°–45°C during the addition period and then is heated at 50°C for 1 hour by circulating hot water through the reactor jacket. The reaction mixture becomes very thick during this period. The reaction is cooled to 20°C and 500 ml of chloroform and 500 ml of water are added. Chlorine is then passed into the reaction mixture through a gas inlet tube reaching to the bottom of the reactor until approximately 284 grams (4.0 moles) of chlorine have been absorbed. The reaction temperature is controlled below 25°C by circulating ice water through the reactor jacket. At the end of the chlorine addition, the chloroform layer is separated and the aqueous layer neutralized with 20% sodium hydroxide, treated with sodium hypochlorite until bleaching of pH paper persists and then discarded. The chloroform layer is stirred into 2,000 grams of 5% sodium hydroxide for 10 minutes and the chloroform layer separated and discarded. The aqueous layer is transferred to a 4 liter beaker and acidified to a pH of 1–2 with concentrated HCl. The product precipitates out of solution upon acidification, is filtered off, washed with 2 liters of water, filtered and air dried. The white solid weighed 337 grams (65% yield) after drying and melted with decomposition at 80°C. The infrared spectrum of the product was consistent with the structure of the proposed compound.

4-t-Butylazo-4-cyanovaleric has a 10 hour half-life at 73°C in water and at 76°C in trichlorobenzene. It cured the unsaturated polyester-styrene resin of Example III at 180°F (82°C) and 212°F (100°C) at a 1.0 weight percent loading giving peak exotherms of 410°F (210°C) and 422°F (217°C) in 8.5 and 3.8 minutes respectively. The cured samples were very hard. The styrene polymerization rates at 5 and 10% conversion for 4-t-butylazo-4-cyanovaleric acid at 85°C were 11.95 × 10⁻³ moles per liter per minute and 11.05 × 10⁻³ moles per liter per minute respectively using the method described for low conversion polymerization in Example II.

EXAMPLE XI

Emulsion Polymerization of Ethyl Acrylate with 4-t-Butylazo-4-cyanovaleric Acid and its Sodium Salt An emulsion containing 50 grams of deionized water, 40 grams of ethyl acrylate, 4.8 grams Triton X-200 (Rohm and Haas anionic surfactant) and 0.0769 grams (3.65 × 10⁻⁴ moles) 4-t-butylazo-4-cyanovaleric acid (from Example X) was prepared. Approximately 25 grams of the emulsion was placed in a 250 ml 4-neck round bottom flask equipped with a mechanical stirrer, thermometer and condenser. Nitrogen was passed through the system and the contents of the flask were heated to the reflux temperature of 82°C. When the temperature rose to 90°C, indicating polymerization was occurring, the balance of the emulsion was slowly added from a self-venting addition funnel, maintaining the temperature at 85°–87°C. At the end of the addition, the temperature was raised to 95°C for 5 minutes, a very small amount of hydroquinone added and the reaction cooled to room temperature. The total reaction time was 1 ⅓ hours. The final pH was 3.6. A 5 gram aliquot was weighed into a tared dish and the monomers and water evaporated and the conversion of monomer to polymer was determined to be 94%.

A similar polymerization was run under the same conditions using $3.65 \times 10^{-4}$ moles of the sodium salt of 4-t-butylazo-4-cyanovaleric acid as the initiator. The conversion was 92.3% and the final pH was 6.6.

A similar polymerization run under the same conditions for 3 hours with no initiator gave only 3 ½% conversion.

EXAMPLE XII

Preparation of 2-t-Cumylazo-2-cyanopropane

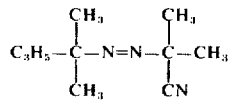

A. Acetone t-cumylhydrazone was prepared according to the method of Overberger (Overberger and Di-Guilio, J. Am. Chem. Soc. 81, 2154 (1959)).

B. 2-t-Cumylhydrazo-2-cyanopropane

The t-cumylhydrazone of acetone (19.0g) was treated with anaqueous solution of excess hydrocyanic acid at R.T. This mixture was stirred for 6 hours and then allowed to stand overnight. The reaction mixture was then extracted with methylene chloride. The methylene chloride extracts were dried over anhydrous sodium sulfate, filtered and the methylene chloride evaporated to obtain a product (21.5g) that had an infrared spectrum in accord with the structure of 2-t-cumylhydrazo-2-cyanopropane. The product was used without further purification in the next step.

C. 2-t-Cumylazo-2-cyanopropane

The crude hydrazo product from above (21.4g) was dissolved in 100 ml methylene chloride, 50 ml of water added and the mixture cooled to 0°C. Chlorine was passed into the solution at 0.4g/min. until 7.1g of chlorine had been added. The temperature was held at 0°–3°C. throughout the addition. At the end of the addition the methylene chloride layer was separated, washed twice with saturated, $NaHCO_3$, dried over anhydrous sodium sulfate, filtered and the methylene chloride evaporated leaving 18.6g of crude 2-t-cumylazo-2-cyanopropane. A sample of the crude 2-t-cumylazo-2-cyanopropane (8.75g) was chromatographed through alumina and 6.0g of the pure liquid 2-t-cumylazo-2-cyanopropane was obtained as evidenced by infrared spectroscopy.

2-t-Cumylazo-2-cyanopropane is a thermally sensitive free radical and gas generator. The compound has a 10 hour half-life in trichlorobenzene at 50°C. The styrene polymerization rates at 5% conversion for 2-t-cumylazo-2-cyanopropane at 60°C was $5.04 \times 10^{-3}$ moles per liter per minute using the method described in Example II. At a 1.0 weight percent loading it cured the unsaturated polyester-styrene resin of Example III at 180°F (82°C) giving a peak exotherm of 378°F (192°C) in 1.3 minutes and a very hard cured resin.

EXAMPLE XIII

Preparation of
1-t-Butylazo-1-cyano-1-cyclopropylethane

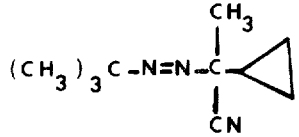

A. t-Butylhydrazone of Methyl Cyclopropyl Ketone

The same procedure as was used in Example VIIA was used for the preparation of methyl cyclopropyl ketone t-butylhydrazone. The yield of liquid product was 8.8g (100%) and the infrared spectrum was consistent with the structure of the proposed compound.

B. 1-t-Butylhydrazo-1-cyano-1-cyclopropylethane

A solution of 8.7g methyl cyclopropyl ketone t-butylhydrazone in 20 ml liquid hydrocyanic acid was heated for 6 hours in a pressure bottle at 60°C. The solution was cooled, poured into ice water and the aqueous solution extracted twice with ether. The ether extracts were combined, washed with saturated sodium bicarbonate solution, dried over sodium sulfate, filtered and the ether evaporated off. The yield was 10.0g (99%) of a brown liquid. The infrared spectrum was consistent with the structure of the proposed product.

C. 1-t-Butylazo-1-cyano-1-cyclopropylethane

To a mixture of 10.0g (.055 m.) of crude 1-t-butylhydrazo-1-cyano-1-cyclopropylethane, 100 ml methylene chloride, and 50 ml water, cooled to 0°C in an ice bath, was added 8.75 g (.055 m.) of bromine dropwise over 15 minutes holding the temperature at 0° to 5°C. After the bromine addition, the reaction was stirred 10 minutes, the methylene chloride layer separated, washed twice with saturated sodium bicarbonate solution, dried over anhydrous sodium sulfate, filtered and the methylene chloride evaporated off. The yield was 8.9g (90%) of a brown liquid. The liquid was chromatographed over an alumina column, eluting it with pentane, to give 8.1g of a light tan liquid which solidifies in the freezer. The infrared spectrum was consistent with the structure of the proposed compound. The product is a thermally sensitive free radical and gas generating compound. The compound has a 10 hour half-life in trichlorobenzene at 62°C.

1-t-Butylazo-1-cyano-1-cyclopropylethane at a 1.0 percent weight loading cured the unsaturated polyester-styrene resin of Example III at 180°F (82.2°C) and 212°F (100°C) giving peak exotherms of 403°F (206.1°C) and 420°F (215.6°C) in 3.3 and 2.1 minutes respectively. The cured samples were very hard.

EXAMPLE XIV

Preparation of 2-t-Amylazo-2-cyanopropane

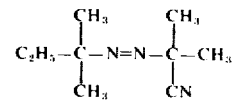

A. t-Amylhydrazine Hydrochloride

An aqueous solution of t-amylhydrazine hydrochloride was prepared by the process described in WL-1320, Ser. No. 684,652. t-Amylurea was chlorinated to form N-t-amyl-N'-chlorourea which was then rearranged in the presence of sodium hydroxide to sodium t-amylhydrazocarboxylate. Acidification with HCl led to decarboxylation and formation of t-amylhydrazine hydrochloride.

B. 2-t-Amylazo-2-cyanopropane

To a solution of 22 grams (.159 moles) of t-amylhydrazine hydrochloride in about 350 ml of water warmed to 37°C in a 500 ml 3-neck round bottom flask equipped with a mechanical stirrer and thermometer was added 7.1 grams (.145 moles) of sodium cyanide followed by 8.4 grams (.145 moles) of acetone. The flask was stoppered and the reaction mixture stirred for 2 ½ hours at 35° ± 3°C and cooled to room temperature. The organic layer was separated, dissolved in 50 ml of pentane and placed back into the 500 ml flask. With rapid stirring 150 ml of an 11% solution of sodium hypochlorite was slowly added to the pentane solution. The temperature slowly rose to 28°C and then slowly dropped back to 25°C. The reaction was stirred an additional 1½ hours at 25°C and the pentane layer separated. The pentane layer was successively washed with water, 10 % HCl, water, 10% $NaHCO_3$, dried over anhydrous sodium sulfate, filtered and the pentane evaporated under reduced pressure, leaving 11.1 grams (46% yield) of a light yellow liquid. The infrared spectrum of the product was in agreement with the structure of the desired azo.

The compound has 10 hour half-life in trichlorobenzene at 79°C. The styrene polymerization rates at 5% and 10% conversion for 2-t-amylazo-2-cyanopropane at 85°C were $10.47 \times 10^{-3}$ moles per liter per minute using the method described for low conversion polymerization in Example II. Using the procedure described in Example III 0.2 grams of 2-t-amylazo-2-cyanopropane cured 20 grams of the unsaturated polyester-styrene resin at 180°F (82°C) in 8.7 minutes. The resultant cured piece was very hard.

EXAMPLE XV

Preparation of 1-t-Amylazo-1-cyanocyclohexane

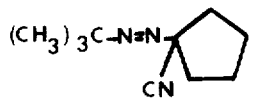

To a solution of 22 grams (0.159 moles) of t-amylhydrazine hydrochloride in about 350 ml of water warmed to 36°C in a 500 ml 3-neck round bottom flask equipped with a mechanical stirrer and theremometer was added 7.1 grams (0.145 moles) of sodium cyanide followed by 14.2 grams (0.145 moles) of cyclohexanone. The flask was stopperred and the reaction mixture stirred for 2½ hours at 35° ± 3°C and cooled to room temperature. The organic layer was taken up in 50 ml of pentane and the aqueous layer separated. The pentane solution was placed back into the 500 ml flask and with rapid stirring 150 ml of an 11% solution of sodium hypochlorite was slowly added to the pentane solution from a dropping funnel. The temperature rose to 35°C so that the reaction was cooled to 30°C with an ice bath. The reaction was stirred an additional 2 hours at 25°–30° C, the pentane layer separated and successively washed with water, 10% HCl, water 10% $NaHCO_3$, dried over anhydrous sodium sulfate, filtered and the pentane evaporated under reduced pressure to leave 22 grams (73% yield) of a light yellow liquid. The infrared spectrum of the product was in agreement with the structure of the desired azo.

1-t-Amylazo-1-cyanocyclohexane has a 10 hour half-life in trichlorobenzene at approximately 94°C. The styrene polymerization rates at 5% and 10% conversion for 1-t-amylazo-1-cyanocyclohexane at 100°C were $14.75 \times 10^{-3}$ moles per liter per minute using the method described for low conversion polymerization in Example II. Using the procedure described in Example III, 1-t-amylazo-1-cyanocyclohexane cured the unsaturated polyesterstyrene resin at 212°F (100°C) in 5.6 minutes and the cured piece was very hard.

EXAMPLES XVI TO XXVIII

The compounds in Table I were prepared in the indicated yield using the procedure described in Example I (method A) or the procedure described in Example V (method B) substituting the proper ketone for the acetone (method A) or cyclohexanone (method B).

TABLE I

| Ex. No. | Name of Compound | Structure of Compound | Starting Ketone | Method | Yield |
|---|---|---|---|---|---|
| XVI | 3-t-butylazo-3-cyanoheptane | $(CH_3)_3C-N=N-\underset{CN}{\overset{C_2H_5}{C}}-(CH_2)_3CH_3$ | 3-heptanone | A | 59% |
| XVII | 2-t-butylazo-2-cyano-3-methylbutane | $(CH_3)_3C-N=N-\underset{CN}{\overset{CH_3}{C}}-CH(CH_3)_2$ | methyl isopropyl ketone | A | 27% |
| XVIII | 2-t-butylazo-2-cyanopentane | $(CH_3)_3C-N=N-\underset{CN}{\overset{CH_3}{C}}-(CH_2)_2CH_3$ | methyl propyl ketone | A | 69% |
| XIX | 3-t-butylazo-3-cyanopentane | $(CH_3)_3C-N=N-\underset{CN}{\overset{C_2H_5}{C}}-C_2H_5$ | diethyl ketone | A | 51% |
| XX | 1-t-butylazo-1-cyanocyclopentane | $(CH_3)_3C-N=N\underset{CN}{\diagup}$ | cyclopentanone | B | 52% |

TABLE I-continued

| Ex. No. | Name of Compound | Structure of Compound | Starting Ketone | Method | Yield |
|---|---|---|---|---|---|
| XXI | 1-t-butylazo-1-cyano-4-methylcyclohexane | $(CH_3)_3C-N=N-\langle cyclohexyl \rangle-CH_3$ with CN | 4-methylcyclohexanone | B | 83% |
| XXII | 1-t-butylazo-1-cyano-3-methylcyclohexane | $(CH_3)_3C-N=N-\langle cyclohexyl \rangle$ with CN, 3-CH_3 | 3-methylcyclohexanone | B | 82% |
| XXIII | 1-t-butylazo-1-cyano-2-methylcyclohexane | $(CH_3)_3C-N=N-\langle cyclohexyl \rangle$ with CN, 2-CH_3 | 2-methylcyclohexanone | B | 72% |
| XXIV | 2-t-butylazo-2-cyanohexane | $(CH_3)_3C-N=N-\underset{CN}{\overset{CH_3}{C}}-(CH_2)_3CH_3$ | methyl butyl ketone | A | 65% |
| XXV | 2-t-butylazo-2-cyano-1-phenylpropane | $(CH_3)_3C-N=N-\underset{CN}{\overset{CH_3}{C}}-CH_2-C_6H_5$ | phenylacetone | A | 90% |
| XXVI | ethyl 3-t-butylazo-3-cyanobutyrate | $(CH_3)_3C-N=N-\underset{CN}{\overset{CH_3}{C}}-CH_2-\overset{O}{\underset{}{C}}OC_2H_5$ | ethyl acetoacetate | A | 31% |
| XXVII | 2-t-butylazo-2-cyano-1-acetoxypropane | $(CH_3)_3C-N=N-\underset{CN}{\overset{CH_3}{C}}-CH_2-O\overset{O}{\underset{}{C}}CH_3$ | acetonyl acetone | A | 24% |
| XXVIII | 2-t-butylazo-2-cyano-5-hydroxypentane | $(CH_3)_3C-N=N-\underset{CN}{\overset{CH_3}{C}}-(CH_2)_3-OH$ | 3-acetyl-1-propanol | A | 75% |

EXAMPLE XXIX

Preparation of 2-t-Butylazo-2-cyano-5-methylhexane

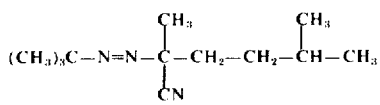

A. t-Butylhydrazone of Methyl Isoamyl Ketone

The t-butylhydrazone of methyl isoamyl ketone was prepared in 95% yield using the same procedure described in Example VIIIA for the preparation of the t-butylhydrazone of diisobutyl ketone, substituting methyl isoamyl ketone for the diisobutyl ketone. The infrared spectrum of the product was consistent with the structure of the desired hydrazone.

B. 2-t-Butylhydrazo-2-cyano-5-methylhexane 2-t-Butylhydrazo-2-cyano-5-methylhexane was prepared in 96% yield using the same procedure described in Example XIIIB for the preparation of 1-t-butylhydrazo-1-cyano-1-cyclopropylethane, substituting the t-butylhydrazone of methyl isoamyl ketone for the t-butylhydrazone of methyl cyclopropyl ketone.

C. 2-t-Butylazo-2-cyano-5-methylhexane 2-t-Butylazo-2-cyano-5-methylhexane was prepared in 94% yield by oxidizing 2-t-butylhydrazo-2-cyano-5-methylhexane with bromine using the same procedure described in Example XIIIC for the oxidation of 1-t-butylhydrazo-1-cyano-1-cyclopropylethane. The crude product was chromatographed over alumina and the product eluted with pentane. The infrared spectrum of the purified product was consistent with the structure of the desired azo. The compound has a 10 hour half-life in trichlorobenzene at approximately 78°C.

EXAMPLE XXX

Preparation of 1-t-Butylazo-1-cyanocyclooctane

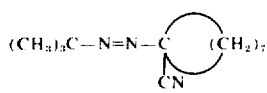

A. t-Butylhydrazone of Cyclooctanone

The t-butylhydrazone of cyclooctanone was prepared in 95% yield using the same procedure described in Example VIIA for the preparation of the t-butylhydrazone of diisobutyl ketone, substituting cyclooctanone for the diisobutyl ketone. The infrared spectrum of the product was consistent with the structure of the desired hydrazone.

B. 1-t-Butylhydrazo-1-cyanocyclooctane 1-t-Butylhydrazo-1-cyanocyclooctane was prepared in 100% yield using the same procedure described in Example XIIIB for the preparation of 1-t-butylhydrazo-1-cyano-1-cyclopropylethane, substituting the t-butylhydrazone of cyclooctanone for the t-butylhydrazone of methyl cyclopropyl ketone.

C. 1-t-Butylazo-1-cyanocyclooctane 1-t-Butylazo-1-cyanocyclooctane was prepared in 93% crude yield by oxidizing 1-t-butylhydrazo-1-cyanocyclooctane with bromine using the same procedure described in Example XIIIC for the oxidation of 1-t-butylhydrazo-1-cyano-1-cyclopropylethane. The crude product was chromatographed over alumina and the product eluted with pentane. The infrared spectrum of the purified product was consistent with the structure of the desired azo. The compound has a 10 hour half-life in trichlorobenzene at approximately 55°C.

EXAMPLE XXXI

Preparation of 1-t-Butylazo-1-cyanocycloheptane

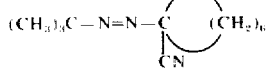

A. t-Butylhydrazone of Cycloheptanone

The t-butylhydrazone of cycloheptanone was prepared in 95% yield using the same procedure described in Example VIIA for the preparation of the t-butylhydrazone of diisobutyl ketone, substituting cycloheptanone for the diisobutyl ketone. The infrared spectrum of the product was consistent with the structure of the desired hydrazone.

B. 1-t-Butylhydrazo-1-cyanocycloheptane 1-t-Butylhydrazo-1-cyanocycloheptane was prepared in 95% yield using the same procedure described in Example XIIIB for the preparation of 1-t-butylhydrazo-1-cyano-1-cyclopropylethane, substituting the t-butylhydrazone of cycloheptanone for the t-butylhydrazone of methyl cyclopropyl ketone.

C. 1-t-Butylazo-1-cyanocycloheptane 1-t-Butylazo-1-cyanocycloheptane was prepared in 100% crude yield by oxidizing 1-t-butylhydrazo-1-cyanocycloheptane with bromine using the same procedure described in Example XIIIC for the oxidation of 1-t-butylhydrazo-1-cyano-1-cyclopropylethane. The crude product was chromatographed over alumina and the product eluted with pentane. The infrared spectrum of the purified product was consistent with the structure of the desired azo. The compound has a 10 hour half-life in trichlorobenzene at approximately 68°C.

EXAMPLE XXXII

Preparation of 2-t-Butylazo-2-cyano-4-methylpentane

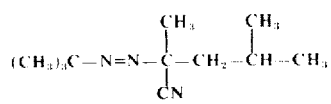

A. t-Butylhydrazone of Methyl Isobutyl Ketone

To a 12 liter, 3-neck round bottom flask seated in a heating mantle was added 7840 grams of an aqueous solution containing 572 grams (6.5 moles) of t-butylhydrazine as an acid salt. The solution was stirred with a mechanical stirrer while 520 grams (6.5 moles) of 50% sodium hydroxide and 610 grams (6.1 moles) of methyl isobutyl ketone were added. The flask was equipped with a thermometer and reflux condenser and the contents were heated to 95°C for 2 hours and then cooled down. The organic layer was separated, dried over anhydrous sodium sulfate, and filtered. The yield was 1027 grams (99% yield).

B. 2-t-Butylazo-2-chloro-4-methylpentane

Into a 5 liter, 4-neck round bottom flask equipped with a low temperature thermometer, a chlorine inlet tube, a mechanical stirrer, and a gas exit tube protected from the atmosphere with a $CaCl_2$ tube, was added 510 grams (3.0 moles) of methyl isobutyl ketone t-butylhydrazone, 303.6 grams (3.0 moles) of triethylamine and 2400 ml of pentane. The contents were cooled to −15°C with a dry ice-isopropanol bath. Then with rapid stirring 213 grams (3.0 moles) of chlorine were passed into the reaction mixture as fast as it was possible to control the temperature at 5°C or below. After all of the chlorine had been added the reaction temperature was adjusted to −5°C to 0°C and the reaction mixture filtered to remove the triethylamine hydrochloride. The triethylamine hydrochloride filter cake was washed with fresh pentane and the filtrate added to the original pentane solution.

C. 2-t-Butylazo-2-cyano-4-methylpentane

A solution of 152 grams (3.1 moles) of sodium cyanide in 1500 ml of 80% aqueous methanol was prepared in a 10 liter 3-neck round bottom flask equipped with a mechanical stirrer, a thermometer and a large dropping funnel. The solution was cooled to 10°C in an ice bath and the pentane solution of 2-t-butylazo-2-chloro-4-methylpentane (from B) added to it at a rate slow enough to maintain the temperature below 15°C. After the addition was complete, the reaction was stirred an additional two hours allowing the temperature to rise to room temperature. The reaction mixture was diluted with 4 liters of water, the pentane layer separated and washed with 300 ml water, 150 ml of 20% HCl, 200 ml water and 200 ml of 10% sodium bicarbonate, dried over anhydrous sodium sulfate, filtered and the pentane evaporated off on a rotating evaporator leaving 500 grams (85% yield) of a light yellow liquid. The infrared spectrum of the product was in agreement with the structure of the desired azo compound. The product was stored at 10°C or below.

2-t-Butylazo-2-cyyano-4-methylpentane has a 10 hour half-life in trichlorobenzene at approximately 70°C. At a 0.5 weight percent loading the above azo cured and unsaturated polyester-styrene resin of Example III at 180°F (82°C) giving a peak exotherm of 394°F (201°C) in 5.7 minutes and a very hard cured resin. In addition, the 2-t-butylazo-2-cyano-4-methylpentane was stable in the resin at room temperature for a period exceeding 1 month. The styrene polymerization rates at 5% and 10% conversion for 2-t-butylazo-2-cyano-4-methylpentane at 70°C were $5.23 \times 10^{-3}$ moles per liter per minute and $4.72 \times 10^{-3}$ moles per liter per minute respectively using the method described for low conversion polymerization in Example II. In the high conversion polymerization of styrene using the procedure described in Example II, $F_1/F_2 = 0.84$ at 70°C (90% conversion) where $F_1$ is 2-t-butylazo-2-cyano-4-methylpentane and $F_2$ is benzoyl peroxide.

EXAMPLE XXXIII

Polymerization of Vinyl Acetate with 2-t-Butylazo-2-cyano-4-methylpentane 2-t-Butylazo-2-cyano-4-methylpentane of Example XXXII was used as an initiator in the polymerization of vinyl acetate using a bottle polymerization technique at autogenous pressures. The formulation used in evaluation is set out below:

| | |
|---|---|
| Vinyl acetate monomer (distilled) | 25 grams |
| Water (distilled) | 100 mls |
| Methocel HG65, 50 cps | 0.24 grams |
| Aerosol MA80 | 0.12 grams |
| 2-t-Butylazo-2-cyano-4-methylpentane | variable |

A water suspension of methocel HG65, and aerosol MA80 was prepared in sufficient quantity to be used in 6 runs. The suspension was then added to a series of six 250 cc short necked bottles according to the above formulation. Twenty-five grams of distilled vinyl acetate monomer was weighed into each of the six bottles. The 2-t-butylazo-2-cyano-4-methylpentane was weighed into tared glass cups in varying amounts from 0.0098 grams to 0.049 grams and the cups placed in their respective bottles. The bottles were flushed with nitrogen for five minutes and securely capped. The bottles placed in a water bath thermostatted at 60°C and the bottles rotated at approximately 30 rpm for 6 hours. At the end of the reaction period, the rotation was stopped and as each bottle was removed from the bath, the cap was immediately loosened to remove any pressure. The bottle was then placed in a 30°C tempering bath. After the bottles had been in the tempering bath 5 minutes, ice was added to cool the contents to 0°C. The polymer was then filtered, washed with distilled water and dried in the vacuum oven at room temperature for 4 hours, 2 hours at 30°C and 1 hour at 50°-60°C. The polymer was weighed and the percent conversion obtained for each bottle by dividing the grams of polymer obtained by 25 and multiplying by 100. It was determined that an 80% conversion was obtained using 0.021 grams of 2-t-butylazo-2-cyano-4-methylpentane per 25 grams of vinyl acetate.

EXAMPLE XXXIV

Preparation of 2-t-Butylazo-2-cyano-4-methoxy-4-methylpentane

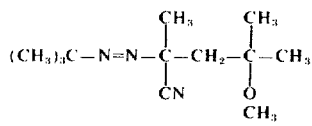

A. t-Butylhydrazone of 4-methoxy-4-methylpentan-2-one

To a 12 liter 3-neck round bottom flask was added 7840 grams of an aqueous solution containing 572 grams (6.5 moles) of t-butylhydrazine as an acid salt. The flask was equipped with a mechanical stirrer, relux condeser and a thermometer and placed in a heating mantle. The contents of the flask were stirred while 520 grams (6.5 moles) of 50% sodium hydroxide and 795 grams (6.1 moles) of 4-methoxy-4-methylpentan-2-one were added. The contents were then heated to reflux for 2 hours and slowly cooled down. The organic layer was separated, dried over anhydrous sodium sulfate, filtered and weighed. The yield was 1160 grams (95% yield).

B. 2-t-Butylazo-2-chloro-4-methoxy-4-methylpentane

Into a 5 liter 4 neck round bottom flask equipped with a low temperature thermometer, a chlorine inlet tube, a mechanical stirrer and a gas exit tube protected from the atmosphere with a calcium chloride tube, was added 800 grams (4.0 moles) of the t-butylhydrazone of 4-methoxy-4-methylpentan-2-one, 404.8 grams (4.0 moles) of triethylamine and 3000 mls of pentane. The contents were cooled to −15°C with a dry ice-isoproponal bath. Then with rapid stirring 284 grams (4.0 moles) of chlorine were passed into the reaction mixture as fast as it was possible to control the temperature at 5°C or below. After all of the chlorine had been added, the reaction temperature was adjusted to −5° to 0°C and the reaction mixture filtered to remove the triethylamine hydrochloride. The triethylamine hydrochloride filter cake was washed with fresh pentane and the filtrate added to the original pentane solution.

C. 2-t-Butylazo-2-cyano-4-methoxy-4-methylpentane

A solution of 206 grams (4.2 moles) of sodium cyanide in 2000 mls of 80% aqueous methanol was prepared in a 12 liter 3 neck round bottom flask equipped with a mechanical stirrer, a thermometer and large dropping funnel. The solution was cooled to 0°C in an ice-salt bath and the pentane solution of 2-t-butylazo-2-chloro-4-methosy-4-methylpentane from step B added to it at a rate slow enough to maintain the temperature below 5°C. After the addition was complete, the reaction was stirred an additional 2 hours allowing the temperature to rise to room temperature. The reaction mixture was then diluted with 6 liters of water, the aqueous layer separated (oxidized with NaOCl to destroy the excess cyanide) and the pentane layer washed successively with 400 ml water, 200 ml 10% HCl, 200 ml 10% NaHCO$_3$, 200 ml water, dried over anhydrous sodium sulfate and filtered. The pentane was evaporated under reduced pressure on a rotating evaporator leaving 805 grams (90% yield) of a yellow liquid. The infrared spectrum of the product was in agreement with the structure of the desired azo compound. The product was stored at 0°C.

2-t-Butylazo-2-cyano-4-methoxy-4-methylpentane has a 10 hour half-life in trichlorobenzene at approximately 55°C. At a 0.5 weight percent loading the above azo cured the unsaturated polyester-styrene resin of Example III at 180°F (82°C) giving a peak exotherm of 354°F (179°C) in 1.4 minutes and a very hard cured resin. The styrene polymerization rates at 5 and 10% conversion for 2-t-butylazo-2-cyano-4-methoxy-4-methylpentane at 60°C were $4.62 \times 10^{-3}$ and $3.96 \times 10^{-3}$ moles per liter per minute respectively using the method described for low conversion polymerization in Example II.

EXAMPLE XXXV

Polymerization of Vinyl Chloride with 2-t-Butylazo-2-cyano-4-methoxy-4-methylpentane 2-t-Butylazo-2-cyano-4-methoxy-4-methylpentane of Example XXXIV was used as an initiator in the polymerization of vinyl chloride using the well-known bottle polymerization technique at autogenous pressures. The formulation used in evaluation is set out below:

| | |
|---|---|
| Vinyl chloride monomer | 100 grams |
| Water (distilled) | 210 ml |
| Methocel* (1500 cps) (1% solution) | 20 ml |
| Sorbitan monostearate (1% solution) | 10 ml |
| Polyoxyethylene sorbitan monostearate (1% solution) | 10 ml |
| 2-t-Butylazo-2-cyano-4-methoxy-4-methylpentane | (variable) |

*A hydroxypropyl methylcellulose product of Dow Chemical.

A water suspension was prepared as set out in the above formulation and added to a 24 ounce beverage bottle which was then frozen at −20°C. A series of bottles was prepared and varying amounts of the initiator added, followed by the freshly distilled vinyl chloride. The bottles were capped and placed in a water bath thermostatted at 50°C. The bath was equipped to cause the rotation of the bottles end over end. After the polymerization had continued at 50°C for 16 hours, the bottles were cooled, vented of excess vinyl chloride monomer, and the yield of polyvinyl chloride determined gravimetrically. It was found that 0.038 grams of 2-t-butylazo-2-cyano-4-methoxy-4-methylpentane were required per 100 grams of vinyl chloride monomer to obtain a 90% conversion to poly(vinyl chloride).

EXAMPLE XXXVI

Preparation of
2-t-Butylazo-2-cyano-5-isobutyroyloxypentane

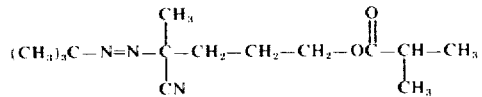

A. 2-t-Butylhydrazo-2-cyano-5-hydroxypentane

To a solution of 7.35 grams (0.05 moles) of 84.3% t-butylhydrazine hydrochloride in 25 mls of water in a 50 ml erlenmeyer flask was added 5.1 grams (0.05 moles) of 3-acetyl-1-propanol and 2.5 grams (0.05 moles) of sodium cyanide and the flask stopperred and stirred overnight. The next morning the organic layer was extracted with methylene chloride, dried over anhydrous Na₂SO₄, filtered and the methylene chloride stripped off. The yield was 10 grams (100% yield) of a light orange liquid. The infrared spectrum of the product was in agreement with the structure of the desired hydrazo compound.

B. 2-t-Butylhydrazo-2-cyano-5-isobutyroyloxypentane

The 2-t-butylhydrazo-2-cyano-5-hydroxypentane (from step A) was dissolved in 40 ml of ether in a 4 neck 100 ml round bottom flask and 7 ml of pyridine and 5.3 grams of isobutyroyl chloride added, holding the temperature below 30°C with a water bath. The reaction mixture was stirred 20 minutes after the addition was over, 25 ml of water added to dissolve the pyridine hydrochloride and the ether layer separated. The ether layer was washed with 25 ml of 10% NaHCO₃, 25 ml of water, dried over anhydrous sodium sulfate, filtered and the ether evaporated under reduced pressure. The yield was 11.4 grams (85% yield) of a light orange liquid. The infrared spectrum of the product was in agreement with the structure of the desired hydrazo compound.

C. 2-t-Butylazo-2-cyano-5-isobutyroyloxypentane

The hydrazo (from step B) was dissolved in 50 ml of methylene chloride and added to 50 ml of water in a 250 ml 3-neck round bottom flask equipped with a thermometer, dropping funnel, condenser and magnetic stirrer. The contents were cooled to 10°C and bromine added dropwise until the red color of the bromine did not disappear. The methylene chloride layer was separated, washed twice with 10% NaHCO₃, once with water, dried over anhydrous sodium sulfate, filtered and the methylene chloride evaporated under reduced pressure leaving 9.4 grams (83% yield) of a light orange liquid. The product was purified by column chromatography over alumina, eluting the product with pentane to give 7.5 grams of 2-t-butylazo-2-cyano-5-isobutyroyloxypentane. The infrared spectrum of the product was in agreement with the structure of the desired azo compound.

The product can also be prepared by esterifying 2-t-butylazo-2-cyano-5-hydroxypentane (Example XXVIII) with isobutyroyl chloride.

EXAMPLE XXXVII

Preparation of
2-t-Butylazo-2-cyano-1-isobutyroyloxypropane

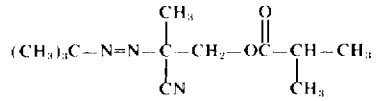

A. 2-t-Butylhydrazo-2-cyanopropanol

To a solution of 5.5 grams (0.0442 moles) of t-butylhydrazine hydrochloride in 25 ml of water cooled to 5°C in a 50 ml erlenmeyer flask equipped with a magnetic stirrer was added 2.94 grams (0.06 moles) of sodium cyanide and 6.56 grams (0.0442 moles) of a 50% aqueous solution of hydroxyacetone. The flask was stopperred, the ice bath removed and the mixture stirred overnight at room temperature. The next morning the mixture was extracted with 50 mls of methylene chloride, the methylene chloride layer separated, washed 3 times with 25 ml portions of 10% NaHCO₃, dried over anhydrous Na₂SO₄, filtered and the methylene chloride evaporated under reduced pressure to leave 7.75 grams (100% yield) of an organge liquid. The infrared spectrum was in agreement with the structure of the hydrazo alcohol.

B. 2-t-Butylhydrazo-2-cyano-1-isobutyroyloxypropane

To a solution of the above hydrazo and 4 grams of pyridine in 50 ml of ether in a 200 ml round bottom flask was added 4.7 grams (0.0444 moles) of isobutyroyl chloride dropwise holding the temperature below 25°C with an ice bath. After the addition was complete, the reaction mixture was stirred for 30 minutes. 25 ml of water added to dissolve the pyridine hydrochloride and the ether layer separated and the ether evaporated under reduced pressure leaving 11.7 grams of wet hydrazo.

C. 2-t-Butylazo-2-cyano-1-isobutyroyloxypropane

The wet hydrazo from step B was dissolved in 25 ml of pentane and transferred to a 150 ml beaker. The hydrazo was then oxidized by slowly adding 0.06 moles of a 10% solution of sodium hypochlorite at 20°C. After the addition was complete the reaction was stirred an additional hour at 25°C, the pentane layer separated, washed with 10% NaHCO₃, twice with 10%

HCl, water, 10% NaHCO$_3$, dried over anhydrous Na$_2$SO$_4$, filtered and the pentane evaporated under reduced pressure to leave 6.35 grams (61% yield) of a yellow liquid. The infrared spectrum of the product was in agreement with the structure of the desired azo. The crude product was purified by column chromatography over alumina and eluting the product with pentane. The pentane was evaporated to leave 4.6 grams of the purified azo.

2-t-Butylazo-2-cyano-1-isobutyroyloxypropane has a 10 hour half-life in trichlorobenzene at approximately 79°C. At a 1 percent weight loading the above azo cured the unsaturated polyester-styrene resin of Example III at 180°F (82°C) in 5 minutes to a very hard resin. The styrene polymerization rates at 5 and 10% conversion for the above azo at 85°C were 8.84 × 10$^{-3}$ and 8.45 × 10$^{-3}$ moles per liter per minute respectively using the method described for low conversion polymerization in Example II.

EXAMPLE XXXVIII

Preparation of
2-t-Amylazo-2-cyano-1-isobutyroyloxypropane

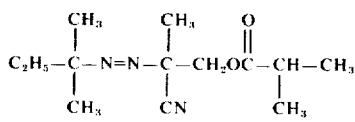

2-t-Amylazo-2-cyano-1-isobutyroyloxypropane was prepared using the same procedure used in Example XXXVII except t-amylhydrazine hydrochloride was used instead of t-butylhydrazine hydrochloride in Step A. The overall yield was 63%. The infrared spectrum of the product was in agreement with the structure of the desired azo.

EXAMPLE XXXIX

Preparation of
2-t-Butylazo-2-cyano-1-benzoyloxypropane

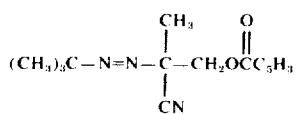

2-t-Butylazo-2-cyano-1-benzoyloxypropane was prepared by acylating 2-t-butylhydrazo-2-cyanopropanol (Example XXXVII A) with benzoylchloride and oxidizing the resultant 2-t-butylhydrazo-2-cyano-1-benzoyloxypropane with sodium hypochlorite using procedures similar to those used in Example XXXVII. The product was a white solid with a melting point of 57°–59°C.

2-t-Butylazo-2-cyano-1-benzoyloxypropane has a 10 hour half-life in trichlorobenzene at approximately 77°C. At a 1 percent weight loading the above azo cured the unsaturated polyester-styrene resin of Example III at 180°F (82°C) in 11 minutes to a very hard resin. The styrene polymerization rates at 5 and 10% conversion for the above azo at 85°C were 2.15 × 10$^{-2}$ and 1.28 × 10$^{-2}$ moles per liter per minute respectively using the method described for low conversion polymerization in Example II.

EXAMPLE XL

Preparation of
2-t-Butylazo-2-cyano-1-pivaloyloxypropane

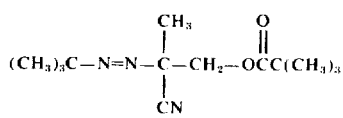

2-t-Butylazo-2-cyano-1-pivaloyloxypropane was prepared by acylating 2-t-butylhydrazo-2-cyanopropanol (Example XXXVIII A) with pivaloyl chloride and oxidizing the resultant 2-t-butylhydrazo-2-cyano-1-pivaloyloxypropane with sodium hypochlorite using procedures similar to those used in Example XXXVIII.

2-t-Butylazo-2-cyano-1-pivaloyloxypropane has a 10 hour half-life in trichlorobenzene at approximately 75°C. At a 1 percent weight loading the above azo cured the unsaturated polyester-styrene resin of Example III at 180°F (82°C) in 5½ minutes to a very hard resin. The styrene polymerization rates at 5 and 10% conversion for the above azo at 85°C were 9.29 × 10$^{-3}$ and 9.29 × 10$^{-3}$ moles per liter per minute respectively using the method described for low conversion polymerization in Example II.

EXAMPLES XLI TO LIV

The general procedure for the preparation of the compounds listed as Examples XLI to LIV in Table II are set out below:

A. Preparation of Ketone t-Butylhydrazones

The ketone t-butylhydrazones, with the exception of acetophenone t-butylhydrazone, were prepared by refluxing an aqueous solution of t-butylhydrazine with the ketone for approximately 2 hours and separating the organic layer after cooling and drying it over anhydrous sodium sulfate. Acetophenone t-butylhydrazone was prepared by azeotrapping off the water from a benzene solution of t-butylhydrazine and acetophenone similar to the preparation of diisobutyl ketone t-butylhydrazone (Example VIIA).

B. Preparation of the α-Chloroazoalkanes

The α-chloroazoalkanes were prepared at 0°–5°C by passing an equimolar equivalent of chlorine into a pentane solution of equimolar equivalents of the t-butylhydrazone and triethylamine and filtering off the triethylamine hydrochloride that formed. The procedure was similar to the (B) steps in Examples XXXII and XXXIV.

C. Preparation of the α-Cyanoazoalkanes of Examples XLI to LIV

The α-cyanoazoalkanes were prepared at 5°–15°C by adding the pentane solution of the α-chloroazoalkanes of step B to an equivalent amount of sodium cyanide in 80% aqueous methanol. The procedure was similar to the (C) steps in Examples XXXII and XXXIV.

TABLE II

| Ex. No. | Name of Compound | Structure of Compound | Starting Ketone | Yield from α-chloro azo | 10 hr. t½ temp. |
|---|---|---|---|---|---|
| XLI | 2-t-butylazo-2-cyano-4,4-dimethylpentane | $(CH_3)_3C-N=N-\underset{CN}{\overset{CH_3}{C}}-CH_2-C(CH_3)_3$<br>m.p. 25°C | methyl neopentyl ketone | 90% | 52°C |
| XLII | 1-t-butylazo-1-cyano-1-phenylethane | $(CH_3)_3C-N=N-\underset{CN}{\overset{CH_3}{C}}-C_6H_5$ | acetophenone | 73% | ~30°C |
| XLIII | 3-t-butylazo-3-cyano-2,2,4,4-tetramethylcyclobutanone | (structure with cyclobutanone ring)<br>m.p. 68–70°C | 2,2,4,4-tetramethylcyclobutandione | 60% | 115°C |
| XLIV | 1-t-butylazo-1-cyano-2,2,4-trimethylcyclopentane<br>and<br>1-t-butylazo-1-cyano-2,4,4-trimethylcyclopentane | (cyclopentane structures) | mixture of 2,2,4-trimethylcyclopentanone<br>and<br>2,4,4-trimethylcyclopentanone | 90% | 84°C |
| XLV | 1-t-butylazo-1-cyano-1-(norborn-2-yl)ethane | $(CH_3)_3C-N=N-\underset{CN}{\overset{CH_3}{C}}$-(norbornyl) | methyl norborn-2-yl ketone | 77%* | — |
| XLVI | 1-t-butylazo-1-cyano-1-(norborn-2-en-5-yl)ethane | $(CH_3)_3C-N=N-\underset{CN}{\overset{CH_3}{C}}$-(norbornenyl) | methyl norborn-2-en-5-yl ketone | 74%* | — |
| XLVII | 1-t-butylazo-1-cyanocyclododecane | $(CH_3)_3C-N=N-\underset{CN}{C}(CH_2)_{11}$ | cyclododecanone | 86% | — |
| XLVIII | 8-t-butylazo-8-cyanotricyclo[5.2.1.0^{2,6}]decane | $(CH_3)_3C-N=N-\underset{CN}{C}$-(tricyclodecane) | 8-keto-tricyclo[5.2.1.0^{2,6}]-decane | 95% | — |
| XLIX | 2-t-butylazo-2-cyanoundecane | $(CH_3)_3C-N=N-\underset{CN}{\overset{CH_3}{C}}-(CH_2)_8-CH_3$ | undecanone | 85% | — |
| L | 1-t-butylazo-1-cyano-2-carbethoxycyclopentane | $(CH_3)_3C-N=N$-(cyclopentane with CN and COOC$_2$H$_5$) | 2-carbethoxycyclopentanone | 52% | — |

TABLE II-continued

| Ex. No. | Name of Compound | Structure of Compound | Starting Ketone | Yield from α-chloro azo | 10 hr. t½ temp. |
|---|---|---|---|---|---|
| LI | 2-t-butylazo-2-cyanooctane | $(CH_3)_3C-N=N-\underset{\underset{CN}{\vert}}{\overset{\overset{CH_3}{\vert}}{C}}-(CH_2)_5-CH_3$ | 2-octanone | 88% | 79°C |
| LII | 2-t-butylazo-2-cyano-5-methyloctane | $(CH_3)_3C-N=N-\underset{\underset{CN}{\vert}}{\overset{\overset{CH_3}{\vert}}{C}}-CH_2-CH_2-\underset{}{\overset{\overset{CH_3}{\vert}}{CH}}-CH_2-CH_2-CH_3$ | 5-methyl-2-octanone | 78% | — |
| LIII | n-butyl 4-t-butylazo-4-cyanovalerate | $(CH_3)_3C-N=N-\underset{\underset{CN}{\vert}}{\overset{\overset{CH_3}{\vert}}{C}}-CH_2-CH_2-\overset{\overset{O}{\Vert}}{C}OC_4H_9$ | n-butyl levulinate | 80% | — |

*Yield from t-butylhydrazone

EXAMPLE LIV

Preparation of 4-t-Amylazo-4-cyanovaleric Acid

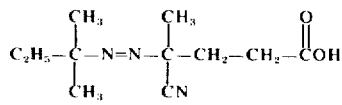

A. 4-t-Amylhydrazo-4-cyanovaleric Acid

To a solution of 16.0 grams (0.01 moles) of 85.5% t-amylhydrazine hydrochloride in 45 ml of water in a 100 ml 4 neck round bottom flask equipped with a thermometer and mechanical stirrer was added 5.9 grams (0.012 moles) of sodium cyanide followed by the dropwise addition of 11.6 grams (0.01 moles) of levulinic acid. The temperature rose to 51°C and the reaction was stirred 4 hours at 50° ± 2°C after the addition was complete and then allowed to stir overnight at room temperature. A thick cream-colored paste formed.

B. 4-t-Amylazo-4-cyanovaleric Acid

The next morning, the above paste was filtered. The filter cake was added to a 250 ml 4-neck round bottom flask equipped with a mechanical stirrer, thermometer and chlorine inlet tube. To the reaction flask was added 20 ml of water and 75 ml of methylene chloride and the contents cooled to 10°C. Chlorine was then passed into the mixture until the exotherm subsided and the aqueous layer bleached pH paper. The reaction mixture was stirred an additional one-half hour and the methylene chloride layer separated. The methylene chloride layer was washed three times with 100 ml portions of distilled water, dried over anhydrous sodium sulfate, filtered and the methylene chloride evaporated under reduced pressure to leave a viscous yellow-orange liquid which slowly solidified. The solid was broken up, slurried in 50 ml of pentane, filtered and air dried to leave 11.7 grams (52% yield) of a white solid melting at 56°-57°C. It assayed 98.8% by neutralization equivalent.

EXAMPLE LV

Preparation of 12-t-Butylazo-12-cyanostearic Acid

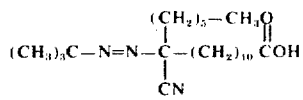

A. t-Butylhydrazone of 12-Ketostearic Acid

A mixture of 45.2 grams (0.066 moles) of a 12.8% aqueous solution of t-butylhydrazine, 18.0 grams (0.06 moles) of 12-ketostearic acid and 10 mls of benzene were heated in a 125 ml flask equipped with a condenser was heated at 95°C for 2 hours. The reaction mixture was cooled, the organic layer separated, dried over anhydrous sodium sulfate, filtered and the benzene evaporated under reduced pressure. The product weighed 21.0 grams (95.2% yield).

B. 12-t-Butylazo-12-cyanostearic Acid

To a solution of 21.0 grams (0.0568 moles) of the t-butylhydrazone of 12-ketostearic acid in 50 ml of pentane, cooled to −20°C, was passed 2.02 grams (0.0285 moles) of chlorine over a 10 minute period. The reaction was stirred an additional 15 minutes at −20°C, the white solid that formed, filtered off, and the pentane filtrate, which should contain approximately 0.0285 moles of 12-t-butylazo-12-chlorostearic acid added to a solution of 1.5 grams (0.03 moles) of sodium cyanide in 20 mls of 75% aqueous methanol. The reaction was stirred for 1 hour at 20°C, poured into 100 ml of water, the pentane layer separated, washed with 5% HCl and then with water until neutral. The pentane solution was dried over anhydrous sodium sulfate, filtered and the pentane evaporated under reduced pressure to leave 8.5 grams (76% yield) of the desired acid.

EXAMPLE LVI

Preparation of 1-t-Cumylazo-1-cyanocyclohexane

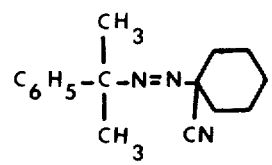

A. t-Cumylhydrazine Sulfate t-Cumylhydrazine sulfate was prepared by acidifying an aqueous solution of t-cumylhydrazine. The t-cumylhydrazine was prepared according to the method of Overberger (Overberger and DiGuilio, J. Am. Chem. Soc. 81, 2154 (1959)).

B. 1-t-Cumylhydrazo-1-cyanocyclohexane hydrochloride

To 188 grams of an aqueous solution containing 12.5 grams (0.0505 moles) of t-cumylhydrazine sulfate warmed to 34°C in a 500 ml 4-neck flask equipped with a thermometer and a magnetic stirrer was added 2.45 grams (0.05 moles) of sodium cyanide followed by 4.9 grams (0.05 moles) of cyclohexanone. The flask was stopperred and the reaction mixture stirred for 3 hours at 30°–35°C, cooled to 20°C and the organic layer extracted with 50 ml of pentane. Concentrated hydrochloric acid was added dropwise to the pentane extract until precipitation of the hydrazo hydrochloride ceased. The hydrazo hydrochloride was filtered, washed with pentane and air dried overnight to give 11.4 grams (78% yield) of a while solid.

C. 1-t-Cumylazo-1-cyanocyclohexane

The above hydrazo hydrochloride was slurried in 90 ml of pentane in a 250 ml round bottom flask and cooled to 5°C. Then 50 ml of water was added and chlorine passed into the system until a slight excess of chlorine was present (bleaching of pH paper by the aqueous phase). The reaction mixture was stirred an additional one-half hour at 10°C, the pentane layer separated, washed with water, 5% HCl, water, 10% NaHCO$_3$, dried over anhydrous sodium sulfate, filtered and the pentane evaporated under reduced pressure to leave 9.5 grams (96% yield) of a yellow liquid. The infrared spectrum of the product was in agreement with the structure of the desired azo.

1-t-Cumylazo-1-cyanocyclohexane has a 10 hour half-life in trichlorobenzene at approximately 62.5°C. At a 1 percent weight loading the above azo cured, the unsaturated polyesterstyrene resin of Example III at 180°F (82°C) in 3 minutes and the cured resin was very hard. The styrene polymerization rates at 5% and 10% conversion for the above azo at 70°C were 2.40 × 10$^{-3}$ and 2.28 × 10$^{-3}$ moles per liter per minute respectively using the method described for low conversion polymerization in Example II. It was determined that 0.15 grams of 1-t-cumylazo-1-cyanocyclohexane were required per 100 grams of vinyl chloride monomer to obtain a 90% conversion to poly(vinyl chloride) using a reaction cycle of 16 hours at 50°C in the suspension polymerization of vinyl chloride as described in Example XXXV.

EXAMPLE LVII

Preparation of 2-t-Cumylazo-2-cyano-4-methylpentane

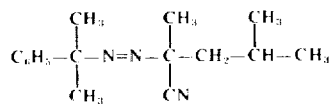

A. t-Cumylhydrazone of Methyl Isobutyl Ketone

The t-cumylhydrazone of methyl isobutyl ketone was prepared in 98% yield by refluxing an 8.9% aqueous solution of t-cumylhydrazine with an equivalent amount of methyl isobutyl ketone for 1 hour, cooling and separating the organic layer.

B. 2-t-Cumylazo-2-chloro-4-methylpentane 2-t-Cumylazo-2-chloro-4-methylpentane was prepared using the same general procedure described for preparing the α-chloro-t-butylazo compounds (Examples XLI to LIII step B).

C. 2-t-Cumylazo-2-cyano-4-methylpentane 2-t-Cumylazo-2-chloro-4-methylpentane was converted to 2-t-cumylazo-2-cyano-4-methylpentane in 70% yield using the same general procedure used for converting the α-chloro-t-butylazo compounds to the corresponding α-cyano azos (Examples XLI to LIII step C). The infrared spectrum was in agreement with the structure of 2-t-cumylazo-2-cyano-4-methylpentane.

2-t-Cumylazo-2-cyano-4-methylpentane has a 10 hour half-life in trichlorobenzene at approximately 33°C. At a 1 percent weight loading the above azo cured the unsatruated polyesterstyrene resin of Example III at 180°F (82°C) in 0.9 minutes and the cured resin was very hard.

EXAMPLE LVIII

Preparation of n-Butyl 4-t-Cumylazo-4-cyanovalerate

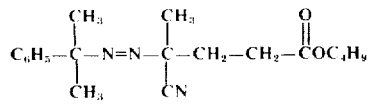

A. t-Cumylhydrazone of n-Butyl Levulinate

The t-cumylhydrazone of butyl levulinate was prepared in 85% yield by refluxing for 2 hours 150 ml of an aqueous solution containing 0.19 moles of t-cumylhydrazine with 31.6 grams (0.184 moles) of n-butyl levulinate, cooling and separating the organic layer.

B. n-Butyl 4-t-Cumylazo-4-chlorovalerate

The n-butyl 4-t-cumylazo-4-chlorovalerate was prepared in 95% yield by passing 7.1 grams (0.1 moles) of chlorine into a 150 ml of pentane containing 32 grams (0.1 moles) of the t-cumylhydrazone of n-butyl levulinate and 10.2 grams (0.1 moles) of triethylamine at −20°C. The triethylamine hydrochloride was filtered off and the pentane filtrate dried and stripped of pentane.

C. n-Butyl 4-t-Cumylazo-4-cyanovalerate

The n-butyl 4-t-cumylazo-4-cyanovalerate was prepared in 90% yield by adding 12.25 grams (0.0346 moles) of n-butyl 4-t-cumylazo-4-chlorovalerate to 30 ml of 75% aqueous methanol containing 1.77 grams (.036 moles) of sodium cyanide using the procedure described for Examples XLI to LIII step C. The product was a yellow liquid and its infrared spectrum was in agreement with the structure of n-butyl 4-t-cumylazo-4-cyanovalerate.

EXAMPLE LIX

Preparation of 4-t-Cumylazo-4-cyanovaleric Acid

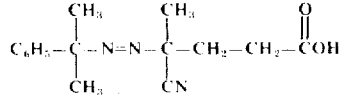

To a stirred solution of 2.8 grams (0.035 moles) of 50% sodium hydroxide in 30 ml of methanol was added 10.7 grams (0.031 moles) of n-butyl 4-t-cumylazo-4-cyanovalerate (from Example LVIII). The reaction mixture was stirred for 3½ hours at room temperature, poured into 150 ml of water and extracted with 50 ml of methylene chloride to remove any unsaponified ester. The aqueous layer was separated, acidified with HCl to a pH of 1 and extracted with 50 ml of methylene chloride. The methylene chloride extract was dried over anhydrous sodium sulfate, filtered and the methylene chloride evaporated under reduced pressure to leave 8.4 grams (94% yield) of a yellow liquid. The infrared spectrum of the product was in agreement with the structure of 4-t-cumylazo-4-cyanovaleric acid.

EXAMPLE LX

Preparation of 3-t-Butylazo-3-cyanobutyric Acid

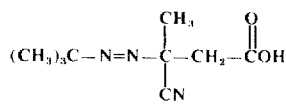

To a stirred solution of 5.6 grams (0.07 moles) of 50% sodium hydroxide in 20 ml of methanol was added 11.25 grams (0.05 moles) of ethyl 3-t-butylazo-3-cyanobutyrate (from Example XXVI). The reaction mixture was stirred for 1 hour at room temperature, poured into 100 ml of water and extracted with 50 ml of pentane to remove any unsaponified ester. The aqueous layer was separated, acidified with HCl to a pH of 1. A solid formed which was filtered off, washed with water and pentane and air dried. The solid weighed 6.0 grams. The infrared spectrum of a nujol mull of the solid was in agreement with the structure of 3-t-butylazo-3-cyanobutyric acid. The melting point was 136°–145°C (dec.).

EXAMPLE LXI

Preparation of 2-t-(Methylcyclohexyl)azo-2-cyanopropane

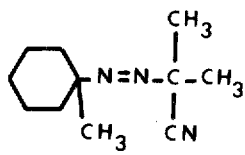

A. t-(Methylcyclohexyl)hydrazine Sulfate

An aqueous solution of t-(methylcyclohexyl)hydrazine sulfate was prepared by the process described in WL-1320, Ser. No. 684,652 t-(methylcyclohexyl)urea was prepared from 1-methylcyclohexanol, urea and sulfuric acid, chlorinated to N-t-(methylcyclohexyl)-N'-chlorourea and then rearranged with sodium hydroxide to sodium t-(methylcyclohexyl)hydrazocarboxylate. Acidification with sulfuric acid led to decarboxylation and formation of t-(methylcyclohexyl)hydrazine sulfate.

B. 2-t-(Methylcyclohexyl)azo-2-cyanopropane

To a 3.8% aqueous solution containing 0.0577 moles of t-(methylcyclohexyl)hydrazine sulfate in a 500 ml 4 neck round bottom flask equipped with a mechanical stirrer and thermometer was added 2.83 grams (0.0577 moles) of sodium cyanide followed by 3.35 grams (0.0577 moles) of acetone. The flask was stoppered and the reaction mixture stirred for 1 hour at 40°C and 2 hours at room temperature. The organic layer was extracted into 50 ml of pentane. The pentane layer was added to a 250 ml 3-neck round bottom flask equipped with a magnetic stirrer, thermometer and dropping funnel. The hydrazo was then oxidized by the slow addition of a sodium hypochlorite solution prepared from 16.0 grams (0.2 moles) of 50% NaOH, 6.3 grams (0.09 moles) of chlorine and 80 ml of water. After the addition was complete, the reaction was stirred overnight at room temperature. The next morning, the pentane layer was separated, washed successively with water, 5% HCl, water, 10% NaHCO$_3$, dried over anhydrous sodium sulfate, filtered and the pentane evaporated under reduced pressure to leave 6.5 grams (59% crude yield) of a dark yellow liquid. The product was purified by column chromatography over alumina and eluting the product with pentane. The infrared spectrum of the purified azo was in agreement with the structure of 2-t-(methylcyclohexyl)azo-2-cyanopropane.

EXAMPLE LXII

Preparation of 1-t-(Methylcyclohexyl)azo-1-cyanocyclohexane

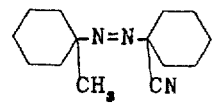

To 240 grams (0.0405 moles) of a 3.8% solution of t-(methylcyclohexyl)hydrazine sulfate in a 300 ml 4-neck round bottom flask equipped with a mechanical stirrer and thermometer was added 1.98 grams (0.0405 moles) of sodium cyanide followed by 3.97 grams (0.0405 moles) of cyclohexanone. The flask was stoppered and the reaction mixture stirred for 3 hours at room temperature. A yellow solid formed during this period. The solid was filtered off and pulled semi-dry. The solid was slurried in 50 ml of pentane in a 250 ml 3-neck round bottom flask equipped with a magnetic stirrer and thermometer and the hydrazo oxidized by the slow addition of a sodium hypochlorite solution prepared from 16.0 grams (0.2 moles) of 50% sodium hydroxide, 6.3 grams (0.09 moles) of chlorine and 80 ml of water. After the addition was complete, the reaction was stirred overnight at room temperature. The next morning, the pentane layer was separated, washed successively with water, 5% HCl, water, 10% NaHCO$_3$, dried over anhydrous sodium sulfate, filtered and the pentane evaporated under reduced pressure to leave 2.5 grams (27% yield) of a light yellow liquid. The infrared spectrum of the product was in agreement with the structure of 1-t-(methylcyclohexyl)azo-1-cyanocyclohexane. The compound has a 10 hour half-life in trichlorobenzene at approximately 100°C.

EXAMPLE LXIII

Preparation of 1-t-Butylazo-1-carbamylcyclohexane

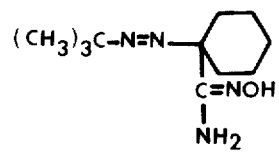

To 100 ml of 95% H$_2$SO$_4$ in a 4 neck 250 ml round bottom flask, cooled to −5°C in a salt-ice bath, was added 23.0 g (0.119 m) of 1-t-butylazo-1-cyanocyclohexane (from Example V) over a one-half hour period holding the temperature between −5° and 0°C during the addition. The temperature was allowed to slowly rise to 20°C over 1 hour, stirred 1 hour at 20°C and finally stirred for 3 hours at 25°C. The acid solution was then added slowly to 750 ml of rapidly stirred cold water, holding the temperature of the water between 10° and 15°C. The reaction was stirred one-half hour and filtered. The filter cake was washed acid free with water and dried. After drying it was slurried in 50 ml pentane and filtered. The yield was 17.3 g of a light yellow solid with a melting range of 86°–92°C (91°–93°C after recrystallization from benzene-pentane). The percent yield was 69%. The pentane filtrate was stripped to dryness leaving 4.4 g of unreacted starting material. The corrected percent yield was 85.5%. The infrared spectrum of the product was consistent with the structure of 1-t-butylazo-1-carbamylcyclohexane.

1-t-butylazo-1-carbamylcyclohexane is a thermally sensitive free radical and gas generator. The compound has a 10 hour half-life in trichlorobenzene at 111°C. It cured the unsaturated-polyester-styrene resin of Example III at a 1.0 weight percent loading at 240°F (115.6°C) giving a peak exotherm of 444°F (228.9°C) in 6.8 minutes.

EXAMPLE LXIV

Preparation of 2-t-Butylazo-2-carbamylpropane

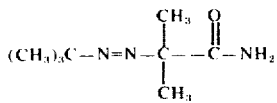

The method of preparing 2-t-butylazo-2-carbamylpropane from 2-t-butylazo-2-cyanopropane (from Example 1) was the same as that used in Example LXIV for the preparation of 1-t-butylazo-1-carbamylcyclohexane. The product was a white solid having a melting range of 80°–82°C. The infrared spectrum of the product was consistent with the structure of 2-t-butylazo-2-carbamylpropane.

2-t-butylazo-2-carbamylpropane is a thermally sensitive free radical and gas generator. The compound has a 10 hour half-life in trichlorobenzene at 110°C. It cured the unsaturated-polyester-styrene resin of Example III at a 1.0 weight percent loading at 240°F (115.6°C) giving a peak exotherm of 442°F (227.8°C) in 5.7 minutes.

EXAMPLE LXV

Preparation of 4-t-Butylazo-4-carbamylvaleric Acid

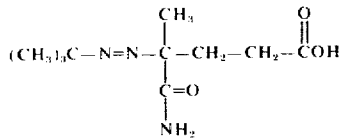

To 20 ml of 95% $H_2SO_4$ cooled to −10°C in a 50 ml round bottom flask immersed in an ice-salt bath, was added 6.0 grams (0.0284 moles) of 4-t-butylazo-4-cyanovaleric acid (from Example X) in small portions over one-half hour holding the temperature at −10°C. After the addition was complete, the mixture was stirred for an additional 4 hours at −5° to −10°C. After 3 hours, the reaction mixture was poured into 75 ml of ice water and the product extracted with 50 ml of methylene chloride. The methylene chloride layer was washed with 100 ml of cold water, dried over anhydrous sodium sulfate, filtered and the methylene chloride evaporated under reduced pressure to leave 4.3 grams (66% yield) of a white-yellow solid. The solid was slurried in 50 ml of pentane, filtered and the filter cake air dried. The purified material had a melting point of 97° −102°C (dec.) and its infrared spectrum was in agreement with the structure of 4-t-butylazo-4-carbamylvaleric acid.

EXAMPLE LXVI

Bottle Suspension Polymerization of Styrene with 2-t-Butylazo-2-cyanopropane 2-t-Butylazo-2-cyanopropane (from Example I) was used as an initiator in the polymerization of styrene using the bottle polymerization technique at autogenous pressures. The formulation used in evaluation is set out below:

| | |
|---|---|
| Distilled Styrene | 25 grams |
| Distilled Water | 50 grams |
| $Ca_3(PO_4)_2$ | 2.5 grams |
| Gelatin (100 bloom type B) | 0.0042 grams |
| 2-t-Butylazo-2-cyanopropane | variable amount from 6.5 × $10^{-4}$ to 16.4 × $10^{-4}$ moles |

A solution of water and gelatin is masterbatched by heating with agitation to 50°C and cooling to room temperature. To each of six indivisual pop bottles was added 50 grams of the water-gelatin solution. The $Ca_3(PO_4)_2$ was weighed and added to each bottle followed by the styrene and 2-t-butylazo-2-cyanopropane. Each bottle was flushed with nitrogen, capped and placed in a water bath thermostatted at 85°C. The bath was equipped to cause the rotation of the bottles end over end. After the polymerization had continued at 85°C for 7 hours, the bottles were cooled slowly to 0°C, the bottles opened and the contents added to 400 ml of methanol. The polystyrene precipitates out of solution, is filtered off and dried in a vacuum oven for 16 hours at 50°C followed by 2–4 hours at 70°C. The polymer product is weighed and the weight of the suspending agents substracted from the weight of the dry product to give the corrected weight of polymer. The percent conversion for each bottle was determined by dividing the corrected weight of polymer by twenty-five and multiplying by 100. The percent conversion was then plotted on a graph vs. concentration of 2-t-butylazo-2-cyanopropane. It was determined that 7.65 × $10^{-4}$ moles of 2-t-butylazo-2-cyanopropane were required to obtain 95% conversion and 12.65 × $10^{-4}$ moles were required to obtain 98.5% conversion.

EXAMPLE LXVII

Preparation of 2-t-Butylazo-2-methylpropionamidoxime

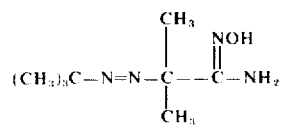

To a mixture of 8.35 grams (0.12 moles) of hydroxylamine hydrochloride and 9.6 grams (0.12 moles) of 50% NaOH in 110 ml of 90% aqueous methanol in a 250 ml round bottom flask equipped with a magnetic stirrer and condenser was added 15.3 grams (0.1 moles) of 2-t-butylazo-2-cyanopropane (from Example I). The mixture was stirred for 72 hours at room temperature, poured into 400 ml of water and extracted with 100 ml of methylene chloride, the organic layer separated, dried over anhydrous sodium sulfate, filtered and the methylene chloride evaporated under reduced pressure leaving a soft solid. The residue was slurried in 100 ml of pentane to remove any unreacted 2-t-butylazo-2-cyanopropane, filtered and the filter cake air dried. The yield was 12.5 grams (67% yield) of a white solid having a melting point of 105°–109°C (dec.). The infrared spectrum of the product was in agreement with the structure of the desired amidoxime.

2-t-Butylazo-2-methylpropionamidoxime has a 10 hour half-life in trichlorobenzene at approximately 90°C. At a 1 percent weight loading the above azo cured the unsaturated polyester-styrene resin of Example III at 212°F (100°C) in 4.6 minutes and the cured resin was very hard.

EXAMPLES LXVIII TO LXXI

The amidoximes of Examples LXVIII to LXXI in Table III were prepared in exactly the same manner as the amidoxime of Example LXVII except 0.1 mole of the indicated α-cyanoazos were used instead of 2-t-butylazo-2-cyanopropane. The reaction period was 10 days at room temperature for Examples LXX and LXXI and the products were purified by low temperature recrystallization from pentane. The recrystallization residue was mostly crude product with a small amount of unreacted starting material.

EXAMPLE LXXII

Preparation of O-Acetyl-2-t-butylazo-2-methylpropionamidoxime

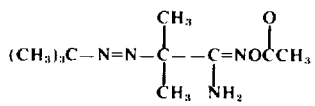

To a solution of 9.3 grams (0.05 moles) of 2-t-butylazo-2-methylpropionamidoxime and 3.96 grams (0.052 moles) of pyridine in 25 ml of methylene chloride in a 3-neck 100 ml round bottom flash equipped with a magnetic stirring bar, thermometer and additional funnel was added a solution of 3.92 gram (.052 moles) of acetyl chloride in 5 ml of methylene chloride dropwise from the additional funnel. The reaction temperature was held at 20°–25°C throughout the addition by an ice bath. The reaction mixture became cloudy and a solid formed near the end of the addition. The reaction mixture was stirred an additional one-half hour at 20°C, the solid filtered off and air dried. The solid weighed 3.0 grams (26% yield) and its infrared spectrum was in agreement with the structure of the N-acetylated product N-acetyl-2-t-butylazo-2-methyl-propionamidoxime. The filtrate was washed with 30 ml of 5% HCl, to remove any unreacted pyridine, water, dried over anhydrous sodium sulfate, filtered and the methylene chloride evaporated under reduced pressure to leave 6.2 grams (54% yield) of a very light yellow solid, m.p. 48°–51°C. The infrared spectrum of this solid was in agreement with the structure of the desired product, O-acetyl-2-t-butylazo-2-methylpropionamidoxime.

At a 1 percent weight loading the above azo cured the unsaturated polyester styrene resin of Example III

TABLE III

| Ex. No. | Name of Compound | Structure of Compound | Starting α-Cyano Azo | Yield | Melting Point |
|---|---|---|---|---|---|
| LXVIII | 2-t-butylazo-2-methylbutyramidoxime | (CH₃)₃C—N=N—C(CH₃)(C₂H₅)—C(NOH)—NH₂ | 2-t-butylazo-2-cyanobutane (from Example VI) | 37% | 67–70°C |
| LXIX | [(1-t-butylazo)cyclohexyl]-carboxamidoxime | (CH₃)₃C—N=N—[cyclohexyl]—C(=O)NH₂ | 1-t-butylazo-1-cyanocyclohexane (from Example V) | 43% | 90–94°C |
| LXX | 2-t-butylazo-2,4-dimethyl-valeramidoxime | (CH₃)₃C—N=N—C(CH₃)(C(=NOH)NH₂)—CH₂—CH(CH₃)—CH₃ | 2-t-butylazo-2-cyano-4-methylpentane (from Ex. XXXII) | 41% | 64–67°C |
| LXXI | 2-t-butylazo-2,4-dimethyl-4-methoxy-valeramidoxime | (CH₃)₃C—N=N—C(CH₃)(C(=NOH)NH₂)—CH₂—C(CH₃)(OCH₃) | 2-t-butylazo-2-cyano-4-methoxy-4-methylpentane (from Example XXXIV) | 30% | 64–68°C |

EXAMPLE LXXIII

Preparation of
O-Benzoyl-2-t-butylazo-2-methylpropionamidoxime

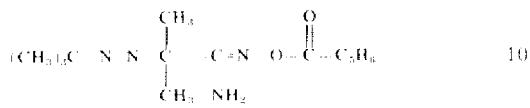

To a solution of 9.3 grams (0.05 moles) of 2-t-butylazo-2-methylpropionamidoxime and 3.8 grams (0.05 moles) of pyridine in 25 ml of methylene chloride in a 3-neck 100 ml round bottom flask equipped with a magnetic stirring bar, thermometer and additional funnel was added a solution of 7.0 grams (0.05 moles) of benzoyl chloride in 5 ml of methylene chloride dropwise from the additional funnel. The reaction temperature was held at 20°–25°C throughout the addition by an ice bath. The reaction mixture was stirred an additional one-half hour at 20°C and filtered. The filtrate was washed with 25 ml of 5% HCl and 25 ml of saturated NaHCO₃ solution, dried over anhydrous sodium sulfate, filtered and the methylene chloride evaporated under reduced pressure to leave 13.5 grams (93% yield) of a light yellow solid, m.p. 112°–116°C. The infrared spectrum of the product was in agreement with the structure of O-benzoyl-2-t-butylazo-2-methylpropionamidoxime.

EXAMPLE LXXIV

Preparation of
O-(Propoxycarbonyl)-2-t-butylazo-2-methylpropionamidoxime

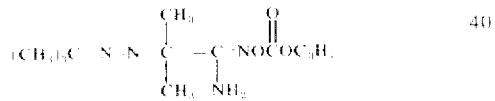

To a solution of 9.3 grams (0.05 moles) of 2-t-butylazo-2-methylpropionamidoxime and 3.8 grams (0.05 moles) of pyridine in 25 ml of methylene chloride in a 3-neck 100 ml round bottom flask equipped with a magnetic stirring bar, thermometer and addition funnel was added a solution of 6.1 grams (0.05 moles) of n-propyl chloroformate in 5 ml of methylene chloride dropwise from the addition funnel. The reaction temperature was held at 20°–25°C throughout the addition by an ice bath. The reaction mixture was stirred an additional one-half hour at 20°C and filtered. The filtrate was washed with 25 ml of 5% HCl and 25 ml of saturated NaHCO₃ solution, dried over anhydrous sodium sulfate, filtered and the methylene chloride evaporated under reduced pressure to leave a light yellow viscous liquid. The flask containing the viscous liquid was placed in the freezer and upon standing overnight, the liquid solidified. The solid was broken up, dissolved in pentane and crystallized out of the pentane in the freezer to give 7.8 grams (57% yield) of a light yellow solid, m.p. 42°–47°C. The infrared spectrum of the product was in agreement with the structure of O-(propoxycarbonyl)-2-t-butylazo-2-methylpropionamidoxime.

EXAMPLE LXXV

Preparation of
O-(Cyclohexyloxycarbonyl)-2-t-butylazo-2-methylpropionamidoxime

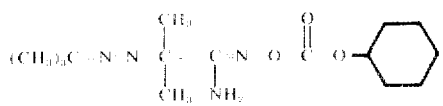

To a solution of 9.3 grams (0.05 moles) of 2-t-butylazo-2-methylpropionamidoxime and 3.8 grams (0.05 moles) of pyridine in 25 ml of methylene chloride in a 3 neck 100 ml round bottom flask equipped with a magnetic stirring bar, thermometer and addition funnel was added a solution of 8.8 grams (0.05 moles) of cyclohexyl chloroformate in 5 ml of methylene chloride dropwise from the addition funnel. The reaction temperature was held at 20°–25°C throughout the addition by an ice bath. The reaction mixture was stirred an additional one-half hour at 20°C and filtered. The filtrate was washed with 25 ml of 5% HCl and 25 ml of saturated NaHCO₃ solution, dried over anhydrous sodium sulfate, filtered and the methylene chloride evaporated under reduced pressure to leave 14.1 grams (90.5% yield) of a light yellow solid that melts at 87°C with decomposition. The infrared spectrum of a nujol mull of the product was in agreement with the structure of O-(Cyclohexyloxycarbonyl)-2-t-butylazo-2-methylpropionamidoxime.

What is claimed is:

1. A compound having the formula

where:

a. $R''$ is alkyl of 1–13 carbons, aralkyl of 7–12 carbons or phenyl, not more than one $R''$ being phenyl;

b. $R_1$ and $R_2$ are alkyl or substituted alkyl of 1–20 carbons, cycloalkyl or bicycloalkyl of 3–10 carbons or, taken together, form an alkylene diradical of 2–16 carbons, and $R_2$ can also be phenyl or substituted phenyl, the alkyl and phenyl substituents being selected from lower alkoxy, phenoxy, lower alkyl-substituted phenoxy, carboxy, hydroxy, lower alkoxycarbonyl, phenylcarbonyloxy, lower alkylcarbonyloxy, halogen, cyano and lower alkylsulfonato, and the phenyl substituents being further selected from lower alkyl; and c. $Z$ is —CN, —C(O)NH₂ or —C(NOH)NH₂.

2. A compound as in claim 1 wherein the $R_1$ and $R_2$ groups are unsubstituted.

3. A compound as in claim 1 wherein the alkyl and phenyl substituents in (b) are selected from carboxy and lower alkoxy and $Z$ is —CN.

4. A compound as in claim 1 wherein the alkyl and phenyl substituents in (b) are selected from lower alkoxy, phenoxy or lower alkyl-substituted phenoxy.

5. A compound as in claim 1 wherein $Z$ is —CN or —C(O)NH₂ and the alkyl and phenyl substituents in (b) are carboxy.

6. A compound as in claim 1 wherein $Z$ is —CN.

7. A compound as in claim 3 wherein (R")₃C— is t-butyl or t-cumyl.

8. A compound as in claim 3 wherein said compound is 2-t-butylazo-2-cyanopropane.

9. A compound as in claim 4 wherein said compound is 1-t-butylazo-1-cyanocyclohexane.

10. A compound as in claim 3 wherein said compound is 4-t-butylazo-4-cyanovaleric acid.

11. A compound as in claim 3 wherein said compound is 2-t-butylazo-2-cyanobutane.

12. A compound as in claim 3 wherein said compound is 2-t-butylazo-2-cyano-4-methylpentane.

13. A compound as in claim 3 wherein said compound is 2-t-butylazo-2-cyano-4-methoxy-4-methylpentane.

* * * * *

UNITED STATES PATENT OFFICE
CERTIFICATE OF CORRECTION

Patent No. 3,931,143          Dated January 6, 1976

Inventor(s) Ronald Edward MacLeay, Chester Stephen Sheppard

It is certified that error appears in the above-identified patent and that said Letters Patent are hereby corrected as shown below:

Column 57, Claim 9 should read as follows:

9. A compound as in claim 3 wherein said compound is 1-t-butylazo-1-cyanocyclohexane.

Signed and Sealed this eleventh Day of May 1976

[SEAL]

Attest:

RUTH C. MASON
Attesting Officer

C. MARSHALL DANN
Commissioner of Patents and Trademarks